US008657877B2

(12) United States Patent
Glazier

(10) Patent No.: US 8,657,877 B2
(45) Date of Patent: Feb. 25, 2014

(54) MULTI-FOCAL PROSTHESIS, AND METHODS FOR MAKING AND USING SAME

(75) Inventor: Alan N. Glazier, Rockville, MD (US)

(73) Assignee: Vision Solutions Technologies, Inc., Rockville, MD (US)

(*) Notice: Subject to any disclaimer, the term of this patent is extended or adjusted under 35 U.S.C. 154(b) by 530 days.

(21) Appl. No.: 12/047,164

(22) Filed: Mar. 12, 2008

(65) Prior Publication Data

US 2010/0211167 A1 Aug. 19, 2010

Related U.S. Application Data

(63) Continuation-in-part of application No. PCT/US2006/044245, filed on Nov. 14, 2006.

(60) Provisional application No. 60/906,505, filed on Mar. 13, 2007, provisional application No. 60/735,879, filed on Nov. 14, 2005.

(51) Int. Cl.
*A61F 2/16* (2006.01)

(52) U.S. Cl.
USPC ........................................ 623/6.13; 623/6.22

(58) Field of Classification Search
USPC ............. 623/4.1, 5.11, 6.13, 6.37, 6.22, 6.27, 623/6.24, 6.34
See application file for complete search history.

(56) References Cited

U.S. PATENT DOCUMENTS

| 2,437,642 | A | 3/1948 | Henroteau |
| 2,714,721 | A | 9/1955 | Stone |
| 2,834,023 | A | 5/1958 | Lieb |
| 3,598,479 | A | 8/1971 | Wright et al. |
| 3,614,215 | A | 10/1971 | Mackta |
| 3,673,616 | A | 7/1972 | Fedorov et al. |
| 3,711,870 | A | 1/1973 | Deitrick |
| 3,866,249 | A | 2/1975 | Flom |
| 3,906,551 | A | 9/1975 | Otter |
| 3,913,148 | A | 10/1975 | Potthast |
| 3,971,073 | A | * | 7/1976 | Richards et al. ............. 623/6.51 |

(Continued)

FOREIGN PATENT DOCUMENTS

| FR | 1279252 | 12/1961 | |
| WO | WO 02/100300 | * 12/2002 | ................ A61F 2/16 |
| WO | WO 2004/054471 A2 | 7/2004 | |

OTHER PUBLICATIONS

Examination Report for corresponding EP Application No. 06837602.9, Jun. 12, 2013, 4pages.

(Continued)

*Primary Examiner* — Paul Prebilic
(74) *Attorney, Agent, or Firm* — Berenato & White, LLC

(57) ABSTRACT

A prosthesis is provided, which includes anterior and posterior lenses spaced from one another and aligned along an optical axis, and an optic body supporting the lenses in spaced relation to one another to establish a chamber between the lenses. Optically transmissive primary and secondary fluids are contained in the chamber. Orienting the optical axis in a horizontal orientation for far vision positions the optical axis through the primary fluid. Orienting the optical axis for near vision at a range of effective downward angles relative to the horizontal orientation positions the optical axis to extend through the primary fluid and the secondary fluid. The prosthesis may further include an internal plate between the lenses, which may be offset at an oblique angle relative to perpendicular to the optical axis. Related methods are also provided.

23 Claims, 14 Drawing Sheets

(56) References Cited

U.S. PATENT DOCUMENTS

| | | | | |
|---|---|---|---|---|
| 4,010,496 | A | 3/1977 | Neefe | |
| 4,174,156 | A | 11/1979 | Glorieux | |
| 4,373,218 | A | 2/1983 | Schachar | |
| 4,477,158 | A | 10/1984 | Pollock et al. | |
| 4,512,040 | A | 4/1985 | McClure | |
| 4,636,211 | A | 1/1987 | Nielsen et al. | |
| 4,709,996 | A | 12/1987 | Michelson | |
| 4,710,193 | A | 12/1987 | Volk | |
| 4,720,286 | A | 1/1988 | Bailey et al. | |
| 4,731,078 | A * | 3/1988 | Stoy et al. | 623/6.13 |
| 4,731,079 | A | 3/1988 | Stoy | |
| 4,932,966 | A | 6/1990 | Christie et al. | |
| 4,994,058 | A | 2/1991 | Raven et al. | |
| 4,995,880 | A * | 2/1991 | Galib | 623/6.13 |
| 5,071,207 | A * | 12/1991 | Ceglio et al. | 359/15 |
| 5,089,023 | A * | 2/1992 | Swanson | 623/6.25 |
| 5,192,318 | A | 3/1993 | Schneider et al. | |
| 5,275,623 | A * | 1/1994 | Sarfarazi | 623/6.13 |
| 5,344,448 | A | 9/1994 | Schneider et al. | |
| 5,354,335 | A | 10/1994 | Lipshitz | |
| 5,443,506 | A * | 8/1995 | Garabet | 623/6.13 |
| 5,522,891 | A | 6/1996 | Klaas | |
| 5,628,798 | A | 5/1997 | Eggleston et al. | |
| 5,683,457 | A | 11/1997 | Gupta et al. | |
| 5,728,156 | A * | 3/1998 | Gupta et al. | 623/6.26 |
| 5,877,839 | A | 3/1999 | Portney | |
| 5,895,422 | A * | 4/1999 | Hauber | 623/6.31 |
| 6,176,878 | B1 | 1/2001 | Gwon et al. | |
| 6,197,059 | B1 | 3/2001 | Cummings | |
| 6,210,438 | B1 | 4/2001 | Sheets, Jr. et al. | |
| 6,450,642 | B1 | 9/2002 | Jethmalani et al. | |
| 6,592,621 | B1 * | 7/2003 | Domino | 623/6.37 |
| 6,663,240 | B2 | 12/2003 | Patel | |
| 6,715,876 | B2 * | 4/2004 | Floyd | 351/159 |
| 6,855,164 | B2 | 2/2005 | Glazier | |
| 7,229,475 | B2 * | 6/2007 | Glazier | 623/6.13 |
| 2002/0052652 | A1 | 5/2002 | Schachar | |
| 2003/0093149 | A1 | 5/2003 | Glazier | |
| 2003/0105522 | A1 | 6/2003 | Glazier | |
| 2003/0208267 | A1 | 11/2003 | Buzard | |
| 2005/0071002 | A1 | 3/2005 | Glazier | |
| 2005/0119739 | A1 * | 6/2005 | Glazier | 623/6.13 |
| 2006/0229720 | A1 | 10/2006 | Glazier et al. | |
| 2007/0067030 | A1 | 3/2007 | Glazier et al. | |
| 2008/0300680 | A1 * | 12/2008 | Joshua | 623/6.37 |

OTHER PUBLICATIONS

Supplemental European Search Report and Examination for EP 06837602.9.

* cited by examiner

MULTI-FOCAL PROSTHESIS, AND METHODS FOR MAKING AND USING SAME

CROSS-REFERENCE TO RELATED APPLICATIONS

This is a continuation in part of PCT International Application No. PCT/US2006/044245 filed Nov. 14, 2006, which claims the benefit of priority of provisional application 60/735,879 filed on Nov. 14, 2005.

This application claims the benefit of priority of U.S. provisional application 60/906,505 filed on Mar. 13, 2007 and U.S. provisional application 60/735,879 filed on Nov. 14, 2005, the complete disclosures of which are incorporated herein by reference.

FIELD OF THE INVENTION

The present invention in certain embodiments relates generally to a prosthesis, and the use of a prosthesis for treatment of retinal degenerative conditions (e.g., low vision, macular degeneration) and other conditions and surgical procedures involving the eyes, especially human eyes, including aphakia, pseudophakia, anterior cortical cataract extraction (acce), posterior cortical cataract extraction (pcce), accommodative restorative surgery for presbyopes, and refractive correction surgery.

BACKGROUND OF THE INVENTION

Generally, the most outwardly visible structures of the human eye include an optically clear anterior cornea, the iris sphincter sitting behind the cornea, and the iris aperture, which is referred to as the pupil. The pupil appears as a circular opening concentrically inward of the iris. Light passes through the pupil along a path to the retina in the back of the eye. In a healthy human eye, a physiological crystalline lens in a capsular bag is positioned posterior to the iris. The chamber between the posterior cornea and the front surface of the capsular bag is commonly referred to as the anterior chamber. A posterior chamber is the area behind the anterior chamber, and includes the capsular bag and physiological crystalline lens.

Ciliary muscle concentrically surrounds the capsular bag, and is coupled to the physiological crystalline lens by suspensory ligaments, also known as zonules. Vitreous humor is contained in the posterior chamber behind the capsular bag. The vitreous humor is surrounded by the retina, which is surrounded by the sclera. The functions and interrelationship of these structures of the human eye are well known in the art and, for this reason, are not elaborated upon in detail herein, except as needed or useful for facilitating an understanding of this invention.

Light entering the emmetropic human eye is converged towards a point focus on the retina known as the fovea. The cornea and tear film are responsible for the initial convergence of entering light. Subsequent to corneal refraction, the incoming light passes through the physiological crystalline lens, where the light is refracted again, towards a point image on the fovea. The amount of bending to which the light is subjected is termed the refractive power. The refractive power needed to focus on an object depends upon how far away the object is from the principle planes of the eye. More refractive power is required for converging light rays to view close objects with clarity than is required for converging light rays to view distant objects with clarity.

A young and healthy physiological lens of the human eye has sufficient elasticity to provide the eye with natural accommodation ability. A young elastic lens may alter its shape, by a process known as accommodation, to change refractive power. The term accommodation refers to the ability of the eye to adjust focus between the distant point of focus, called the Punctum Remotum or pr (far point beyond 20 feet or 6 meters away), and the near point of focus called the Punctum Proximum or pp (near point within 20 feet or 6 meters away from the eye). Focus adjustment is performed in a young elastic lens using the accommodative-convergence mechanism. The ciliary muscle functions to shape the curvature of the physiological crystalline lens to an appropriate optical configuration for focusing and converging light rays entering the eye on the fovea of the retina. It is widely believed that this accommodation is accomplished via contracting and relaxing the ciliary muscles, which accommodate the lens of the eye for near and distant vision, respectively.

More specifically, the eye is "unaccommodated" for far vision by the ciliary muscle relaxing to decrease the convexity of the lens, according to accepted theoretical models of the function of the accommodative mechanism. In this unaccommodated state, the ciliary muscle relaxes. The suspensory zonules holding the lens in place and anchoring it to the ciliary muscle are at their greatest tension. The tension of the zonules causes the lens surfaces to take their flattest curves, making the retina coincident with the far point pr. On the other hand, the ciliary muscle actively accommodates the eye for near vision by increasing the convexity of the lens within the eye via contraction of the muscle. In the accommodated state, the ciliary muscle is constricted in a sphincter-like mode, relaxing the zonules and allowing the lens to take a more convex form. In the fully accommodated state, the retina is coincident with the near point of accommodation pp.

The term emmetropia is understood in the art to mean that natural focus of the optics of the eye when viewing a distant object (greater than 6 meters) is coincident with the retina. The term ammetropia means that the distance focus is displaced from the retina, such as in the case of hypermetropia, astigmatism, and myopia. Hypermetropia denotes an error of refraction caused when the retina intercepts the rays (or pencils) received by the eye before the rays reach their focus. Myopia denotes an error of refraction caused when the pencils within the eye focus to a real point before the pencils reach the retina.

With presbyopia, incoming light rays from the pp are focused at a virtual point situated behind the retina. The ciliary body-zonules-lens complex becomes less efficient at accommodating the focus of these rays on the retina. According to one theory behind presbyopia, the physiological crystalline lens slowly loses its elasticity as it ages. As the physiological crystalline lens ages, the alteration in curvature becomes less for the same action of the ciliary muscle. According to another theory, the physiological lens enlarges with age causing a decrease in working distance between the ciliary body and the lens, resulting in decreased focus ability for the same muscle action. For most people, generally the decline in focusing ability starts in youth and continues until the age of about 60. Generally, it becomes necessary for most people around the age of 40 to use near addition lenses to artificially regain sufficient amplitude at near to accommodate for the pp when attempting to perform near-point activities such as reading. This condition is known as presbyopia, and eventually afflicts almost every human being.

Convergence of the rays in a healthy, phakic (with lens) eye having presbyopia is most commonly achieved with the assistance of eyeglass lenses, contact lenses, or refractive surgery. Once corrected, distance and near objects can be seen clearly.

Aphakia is the condition in which the crystalline lens is either absent or, in very rare cases, displaced from the pupillary area so that it adversely affects the eye's optical focusing system. The former condition may be congenital, but it is usually the result of cataract-removal surgery. With advancing age, the physiological crystalline lens tends to develop opacities—a condition known as cataractogenesis—which unless treated eventually leads to blindness.

In the absence of other pathology or degenerative changes, removal of the opaque crystalline lens afflicted with cataracts restores the possibility of obtaining good vision with refractive implements such as eyeglasses, contact lenses, or intraocular lenses. Pseudophakia describes when the crystalline lens is replaced with a synthetic intraocular lens.

Removal of the crystalline lens by surgery entails the loss of ability to accommodate, so additional positive power in the form of a near addition is needed for near focus. If the synthetic lens is of proper power and results in the pr focusing on the retina, the refractive error for distance will have been eliminated. However, current synthetic intraocular lenses lack the flexibility of a physiological crystalline lens. As a consequence, it is difficult, if not impossible, for the ciliary muscle to focus current synthetic intraocular lenses in the same way as a physiological lens to adjust for objects near the pp. Thus, conventional monofocal intraocular lenses provide little, if any accommodating ability.

Generally, a plus-powered eyeglass lens or contact lens is used in conjunction with an eye having a synthetic intraocular lens to adjust for objects near the pp. Pseudophakic individuals corrected for distance and emmetropia will usually require a lens in front of their eye the equivalent of approximately +2.50 diopters of power to be able to focus on near-point objects between 12 and 20 inches from the eye (approximate). However, "reading" glasses and contact lenses have the drawbacks of being inconvenient, uncomfortable, susceptible to loss and breakage, and in the case of glasses, aesthetically undesirable to some users.

Another problem that adversely affects an individual's eyesight, both near and far, is retinal degenerative condition (RDC). Generally, an RDC involves damage to the macula. An RDC such as macular degeneration leaves the afflicted individual with a "blind spot" or scotoma usually at or near the center of a person's visual field. The afflicted individual is often only able to see peripheral images around the blind spot. The visual field provided by such peripheral images is often insufficient to allow the individual to perform routine activities such as reading, driving a vehicle, or even daily chores and errands. For example, when an individual having a RDC attempts to recognize another person at a distance, the individual may be able to discern the eccentric body portions of the viewed person peripherally, but the scotoma may "wipe out" the facial details of the viewed person, rendering the person unrecognizable.

A person who suffers from a RDC is typically treated optically by using magnification or prism in lens form. A Galilean telescopic magnifying device may be placed in front of the eye or in the eye and customized to the user's needs. The magnification of the device enlarges the image viewed, expanding the image into more healthy areas of retina peripheral (eccentric) to the scotoma. At near, the person suffering from a RDC usually needs magnification in the form of magnifying plus powered lenses and/or prisms—the former (i.e., the plus lenses and magnifiers) to help enlarge the image outside of the scotoma as in the telescopic example and the latter (e.g., the prisms) to help shift the images to different, more functional areas of the retina.

Devices used to provide magnification at distance and near are prescribed according to the art and science of "low-vision". An example of a low vision device for distance use is a spectacle-mounted telescopic device. An example of a low vision device for near use is a hand-held magnification device and/or prism to assist the user in accessing retinal area peripheral to the damaged area responsible for producing the scotoma. Devices used to provide magnification at distance and near have several drawbacks. First of all, the devices are heavy and bulky, making them difficult to use from an ergonomic perspective. Second, the devices, such as those mounted on a pair of spectacles, may be considered aesthetically unappealing by some. Third, telescopic devices outside of the eye cause distortion (e.g., create aberrations, astigmatism), glare, or decrease the effectiveness of magnification, for example, in the case of spectacle-mounted telescopic devices in which there exists a vertex distance (the distance from the back of the lens to the front of the cornea). Fourth, many current implantable telescopic lenses are held within bulky housings, which decrease the user's peripheral vision and result in a significant loss in the user's field of vision. Fifth, in the example of near vision magnification, the devices are often housed in a hand held device, which prevents the user from accessing "hands free" use of the device—e.g., the user may have trouble holding a newspaper or book in one hand and a device in the other.

SUMMARY OF THE INVENTION

A first aspect of the invention features a prosthesis including first and second lenses in alignment with one another, and an optic body supporting the first and second lenses in spaced relation to one another to establish a chamber between the lenses. Optically transmissive primary and secondary fluids are contained in the chamber of the optic body. The primary fluid is immiscible with and has a different density and refractive index than the secondary fluid. The prosthesis further includes an internal plate positioned within the chamber between the first and second lenses, wherein the internal plate has substantially planar, substantially parallel opposite surfaces facing the first and second lenses, respectively.

According to a second aspect of the invention, a method is provided for optically altering an image viewed through a prosthesis, preferably implanted in a human eye. The method features viewing an object through a prosthesis. The prosthesis includes first and second lenses in alignment with one another, and an optic body supporting the first and second lenses in spaced relation to one another to establish a chamber between the lenses. Optically transmissive primary and secondary fluids are contained in the chamber of the optic body. The primary fluid is immiscible with and has a different density and refractive index than the secondary fluid. The prosthesis further includes an internal plate positioned within the chamber between the first and second lenses, wherein the internal plate has substantially planar, substantially parallel opposite surfaces facing the first and second lenses, respectively.

A third aspect of the invention features a prosthesis including at least a positive lens, a negative lens in alignment with and spaced from the positive lens, and an optic body supporting the positive lens and the negative lens in spaced relation to one another to establish a chamber between the lenses. Optically transmissive primary and secondary fluids are contained in the chamber of the optic body. The primary fluid is immiscible with and has a different density and refractive index than the secondary fluid.

According to a fourth aspect of the invention, a method is provided for optically altering an image. The method features viewing an object through the prosthesis. The prosthesis includes at least a positive lens, a negative lens in alignment with and spaced from the positive lens, and an optic body supporting the positive lens and the negative lens in spaced relation to one another to establish a chamber between the lenses. Optically transmissive primary and secondary fluids are contained in the chamber of the optic body. The primary fluid is immiscible with and has a different density and refractive index than the secondary fluid.

In an optional embodiment of the third and fourth aspects, the prosthesis comprises an intraocular lens implantable into a human eye, wherein the positive lens and the negative lens are an objective lens for facing the anterior side and an ocular lens for facing the posterior side of the human eye, respectively. In this embodiment, the objective and ocular lenses optionally are arranged with respect to one another to collectively establish a Galilean system. This embodiment is particularly useful in treatment of persons suffering from low vision disorders and RDCs, causing the viewed image to be enlarged beyond the borders of the damaged retina both in straight ahead gaze and down gaze.

In another embodiment of the above described and other aspect of the invention, lens curvatures and fluids may be selected to increase the power of the prosthesis in down gaze and to enlarge the image viewed in down gaze beyond the damaged region of the retina.

In another optional embodiment of the third and fourth aspects, the prosthesis comprises an intraocular lens implantable into a human eye, wherein the positive lens and the negative lens are an ocular lens for facing the posterior side of the human eye and an objective lens for facing the anterior side of the human eye, respectively. In this embodiment, the objective and ocular lenses optionally are arranged with respect to one another to collectively establish a reverse Galilean system. This embodiment is particularly useful in treatment of conditions characterized by a loss of peripheral field vision, retinitis pigmentosa and glaucoma.

In accordance with the construction of the prosthesis of embodiments of the invention, multi-focus vision may be achieved by the natural motion of the user's eye and/or head. For distant or far vision, the user gazes straight ahead to orient the optical axis substantially parallel to the horizon. In this straight-ahead gaze, the optical axis passes through (or intersects) the optically transmissive primary fluid, but not the secondary fluid. The refractive index of the primary fluid through which the optical axis passes and the curvature of the lenses alter the effective power of the prosthesis for focusing.

In practice, as the natural inclination to view near objects causes the eye to angle downward for near vision, such as in the case for reading, the primary and secondary fluids move relative to the lens body to cause the optical axis (and visual axis) to pass through (or intersect) both the fluids. The combined refractive indexes of the primary and secondary fluids and the curvature of the lenses dictate the effective power of the lens for focusing on near objects (at the pp). Thus, as the eye and/or head tilts downward for reading, the position of the eye and the angle of the optical axis of the prosthesis relative to the horizon changes. This tilting movement alters the power of the lens by intercepting both of the fluids with the optical axis. The effective power of the prosthesis is returned to its original straight ahead state as the optical axis returns to the horizontal orientation and the secondary fluid is removed from interception with the optical axis.

It should be readily apparent that the invention is not limited devices producing telescopic effects. However, in those embodiments of the invention in which a magnifying telescopic effect is established, the telescopic optics preferably magnify the image desired to be viewed beyond the borders of the damaged region of the retina (or macula) which is responsible for the scotoma, i.e., into healthy areas of the central retina. As a consequence, although the scotomatous area is not removed from the field of vision, the viewed object is optically altered, e.g., shifted or magnified, so that a greater percentage of the object is viewed peripheral to (i.e., outside of) the scotoma.

In an exemplary embodiment of this invention, the adjustment in effective power of the prosthesis is achieved without any moving parts (other than the flow of the refractive fluids) and optionally without requiring the division of the prosthesis into separate compartments via internal channels that prevent or substantially inhibit elastic deformation of the prosthesis.

The primary fluid and the secondary fluid may comprise a first liquid and a second liquid, respectively. Alternatively, either of the fluids may be a gas, a mixture of gases, or vacuum. In one variation of this aspect, the first density is greater than the second density. Alternatively, the second density may be greater than the first density.

It is to be understood that the aspects described above are not exclusive or exhaustive of the scope of the invention. Many variations, modifications, and alternative steps and methods to those described above may be practiced.

BRIEF DESCRIPTION OF THE DRAWINGS

The accompanying drawings are incorporated in and constitute a part of the specification. The drawings, together with the general description given above and the detailed description of the exemplary embodiments and methods given below, serve to explain the principles of the invention. In such drawings.

Figure 1:
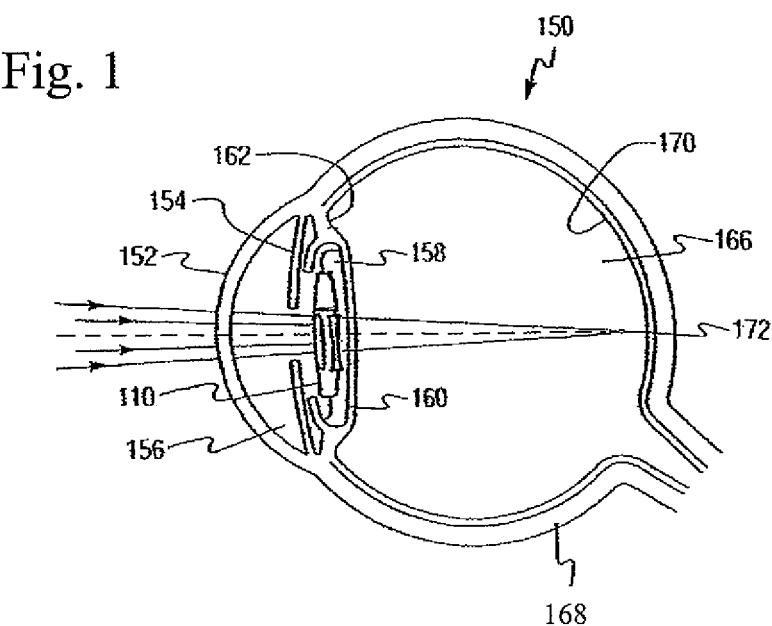
FIG. 1 is a schematic representation of a human eye with a posterior chamber containing a prosthesis in which the eye is gazing straight ahead at the horizon.

DETAILED DESCRIPTION OF THE EXEMPLARY EMBODIMENTS AND EXEMPLARY METHODS OF THE INVENTION

Reference will now be made in detail to the presently exemplary embodiments and methods of the invention as illustrated in the accompanying drawings, in which like reference characters designate like or corresponding parts throughout the drawings. It should be noted, however, that the invention in its broader aspects is not limited to the specific details, representative devices and methods, and illustrative examples shown and described in this section in connection with the exemplary embodiments and methods. The invention according to its various aspects is particularly pointed out and distinctly claimed in the attached claims read in view of this specification, and appropriate equivalents.

It is to be noted that, as used in the specification and the appended claims, the singular forms "a," "an," and "the" include plural referents unless the context clearly dictates otherwise.

FIGS. 1-4 illustrate a prosthesis, which is depicted in several of the drawings as an intraocular lens (IOL), generally designated by reference numeral 110, according to a first exemplary embodiment of this invention. Prosthesis 110 includes an optic body 112, which for the purpose of the IOL illustrated in FIGS. 1-4 is sized and configured to be received in the capsular bag 160 of a human eye 150. Optic body 112 may possess a generally cylindrical shape. In this embodiment, optic body 112 supports a positive objective lens 114, and a negative ocular lens 116 aligned with and spaced behind objective lens 114. A chamber 118 is established between lenses 114, 116 within optic body 112. Chamber 118 is enclosed between lenses 114, 116 within optic body 112, and more particularly is enclosed by a structure consisting of lenses 114, 116 and optic body 112. Lenses 114, 116 may be, for example, either made as a unitary "integral" piece of optic body 112 or may be formed as separate members joined together with optic body 112. An optical axis 120 intersects objective lens 114 at a front vertex and ocular lens 116 at a rear vertex. Lenses 114, 116 are preferably spherical, although each may be aspheric, and may be produced or modified into an aspheric shape or otherwise to compensate for astigmatism, coma, and higher order aberrations, including double images induced by prism.

Figure 22:
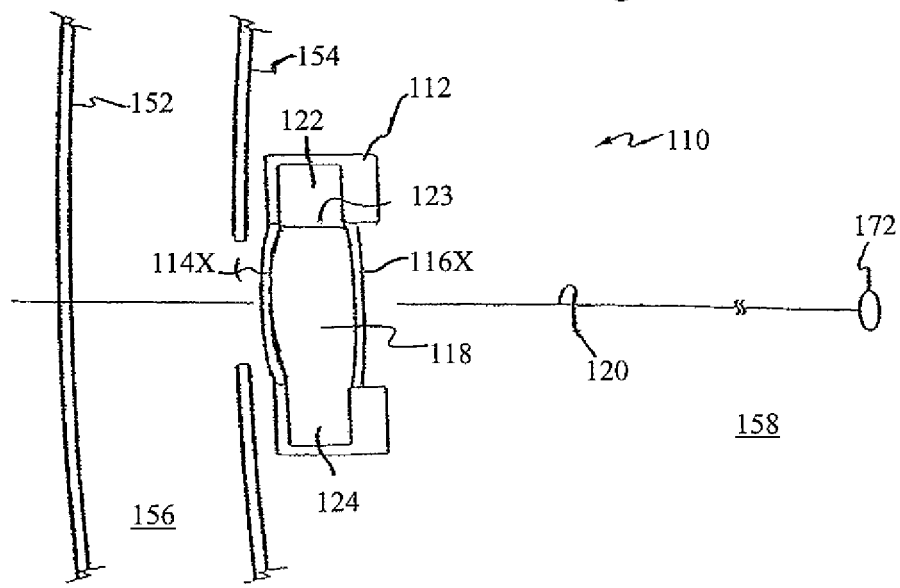
FIG. 22 is a schematic, enlarged view of the prosthesis of another embodiment of the invention, depicting the prosthesis oriented in straight-ahead gaze.
Figure 23:
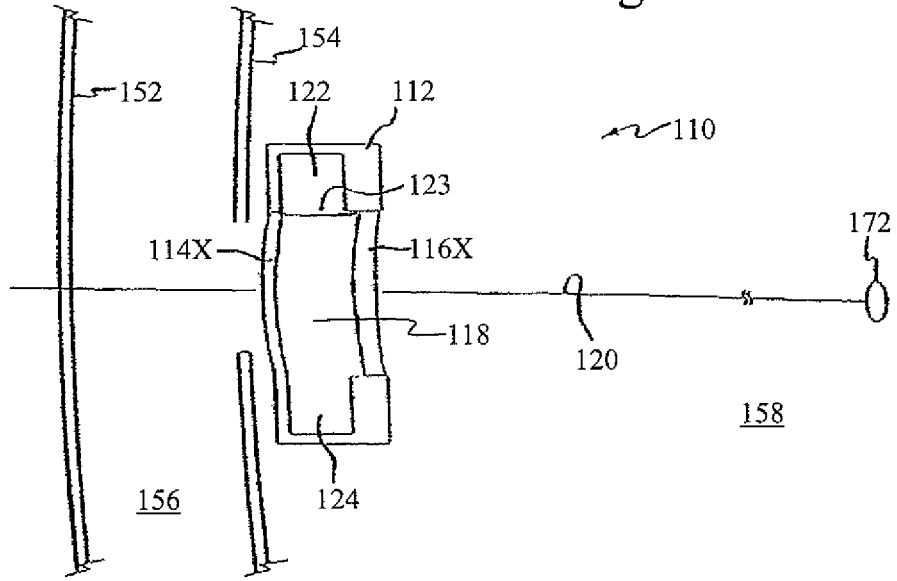
FIG. 23 schematic, enlarged view of the prosthesis of another embodiment of the invention, depicting the prosthesis oriented in straight-ahead gaze.

In the illustrated embodiment of FIGS. 1-4, objective lens 114 is convex-convex (biconvex) and ocular lens 116 is concave-concave (biconcave). It is possible to use alternative combinations depending upon the desired effective power and refractive properties of IOL 110. Additionally, either of lens 114, 116 may have a non-curved or flat surface with a radius of curvature equal to zero, e.g., convex-flat, flat-convex, concave-flat, or flat-concave. Lens 114 and/or 16 may have a combination of convex and concave surfaces, e.g., concave-convex or convex-concave, shaped to provide the desired effective power and refractive properties. For example, FIG. 22 illustrates an embodiment in which lens 114X is convex-concave, and lens 116X is concave-convex. FIG. 23 illustrates and embodiment in which lens 114Y and 116Y are each convex-concave. The illustrated combinations of lenses are not meant to be limiting upon the full scope of the invention.

It is also within the scope of the invention to use multiple objective lenses 114 and/or ocular lenses 116, and/or to have either or both of lenses 114, 116 comprised of laminates. Another possibility is to employ lenses 114, 116 with discrete refractive zones, especially concentric zones, such as in the case of Fresnel magnification. These are just some of the variations encompassed by the full scope of the invention.

Optic body 112 of this first embodiment and other embodiments described herein is optionally, although not necessarily, free of interior and exterior channels, especially those that would prevent the deforming or folding of optic body 112 during surgical insertion.

Chamber 118 of optic body 112 contains an optically transmissive upper fluid 122 and an optically transmissive lower liquid 124. It is possible in this and other embodiments of the invention that upper fluid 122 be a liquid or mixture of liquids, and that the liquids 122 and 124 fill the entire chamber 118, thereby eliminating any gases or free space within the chamber 118. Alternatively, upper fluid 122 may be a gas or mixture of gases, including air, or a vacuum. Lower liquid 124 is denser than and has a different refractive index than upper fluid 122. Upper and lower fluids 122, 124 are substantially immiscible with one another. As referred to herein, substantially immiscible means that upper and lower fluids undergo no or sufficiently small amounts of intermixing so that the function of the refractive fluids is performed, i.e., multi-focal sight is obtained by physical tilting of prosthetic 110.

Figure 2:
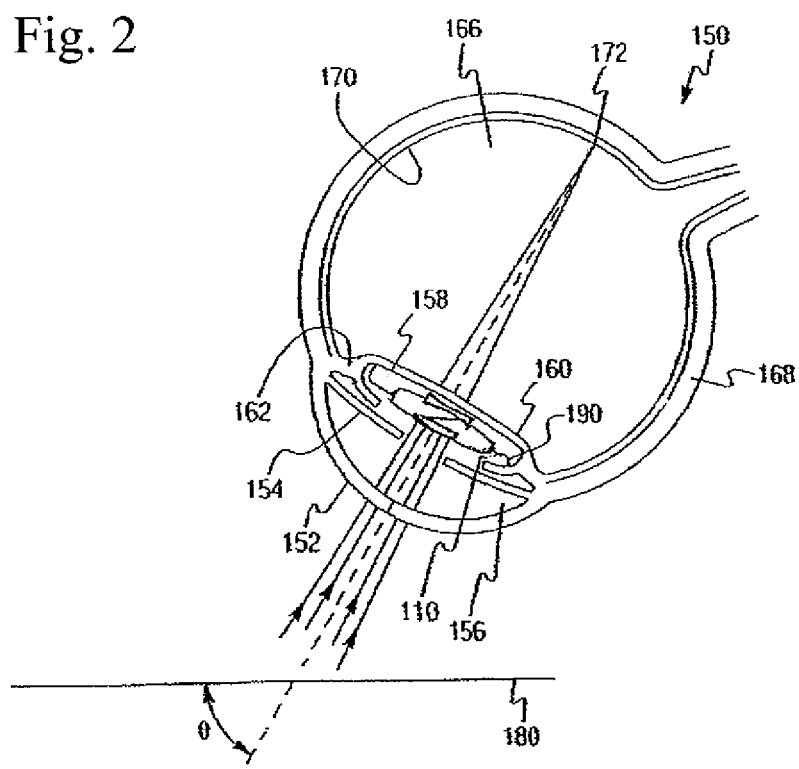
FIG. 2 is a schematic representation of the human eye containing the prosthesis of FIG. 1, in which the eye is angled downward in a reading position.

A simplified schematic of the human eye having prosthetic 110 of this first embodiment implanted in posterior chamber 158 of eye 150 is illustrated in FIGS. 1 and 2. Eye 150 includes optically transmissive cornea 152, behind which is iris 154. The pupil (unnumbered) is interior to iris 154 and commonly appears as a black circular area concentrically inward of iris 154 when viewed from directly in front of eye 150. Posterior chamber 158 of eye 150 includes capsular bag 160, which is shown in this embodiment holding intraocular lens 110. The chamber between cornea 152 and the front surface of capsular bag 160, as shown in FIGS. 1 and 2, is commonly referred to in the art as anterior chamber 156.

Ciliary muscle 162 surrounds capsular bag 160, and is coupled to the physiological crystalline lens by zonules. The physiological crystalline lens is presumed to have been removed in FIGS. 1 and 2 and therefore is not shown. The portion of posterior chamber 158 behind capsular bag 160 contains vitreous humor, which is interior to sclera 168. The conjunctiva (not shown) coats sclera 168. Light entering the human eye is converged on retina 170 at macula 172, via the optics of cornea 152 and intraocular lens 110. In a healthy human eye, as incoming light rays pass through IOL 110, the light rays are bent or refracted to converge at a point at macula 172 of retina 170 to provide a clear image. Other light rays that are incident on retina 170 away from macula 172 are also detected, usually as part of one's peripheral vision.

Optical axis 120 is situated in optic body 112 for placement along a light path 121 that enters through and is initially refracted by cornea 152, then passes through the pupil to retina 170. An optically transmissive anterior visual zone of objective lens 114 defines an area through which the light path intersects lens 114. An optically transmissive posterior visual zone of ocular lens 116 defines an area through which the light path intersects lens 116. Although the visual zones may be coextensive with the outer perimeters of lenses 114, 116, the visual zones are more typically smaller in diameter and concentric with the outer perimeters of lenses 114, 116. If prosthesis 110 is positioned in posterior chamber 156, then incoming light traveling along the light path is refracted by prosthesis 110 subsequent to passing through iris 154. Thus, when prosthesis 110 is in posterior chamber 158, iris 154 functions to filter or block a portion of the light that passes through cornea 152. As referred to herein, the light path through a posterior chamber lens coincides with the portion of the light that enters through the tear film (not shown) and cornea 152, passes through the pupil and is refracted by prosthesis 110 to retina 172. On the other hand, if prosthesis 110 is positioned in anterior chamber 156, incoming light traveling along the light path is refracted by prosthesis 110 before the light passes through the pupil of iris 154. When prosthesis 110 is in anterior chamber 156, iris 154 may filter or block a portion of the light leaving prosthesis 110. As referred to herein, the light path through an anterior chamber lens coincides with the portion of the light that enters through cornea 152, is refracted by the anterior chamber lens and then passes through the pupil to retina 172.

Figure 3:
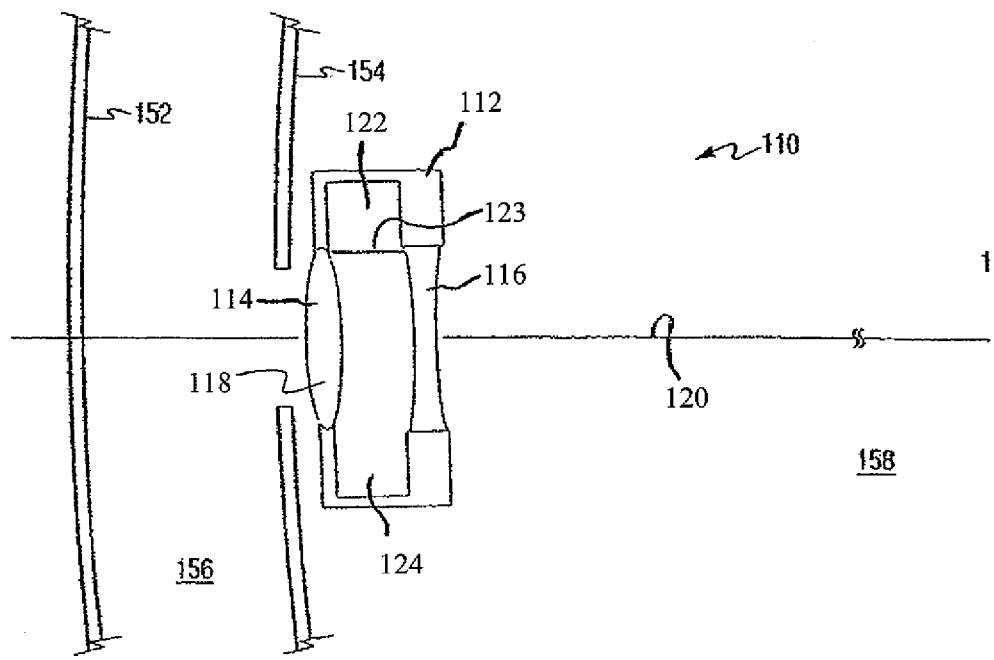
FIG. 3 is a schematic, enlarged view of the prosthesis of a first embodiment of the invention, depicting the prosthesis oriented in straight-ahead gaze.

FIG. 3 shows prosthesis 110 of the first embodiment of this invention positioned in posterior chamber 158 of eye 150 gazing straight ahead at the pr. In this straight-ahead gaze, optical axis 120 is parallel to horizontal plane 180, that is, in a horizontal orientation. (Horizontal plane 180 is shown in FIG. 2. As is understood in the art, the eye is usually not rotationally symmetric, so that the optical axis and the visual axis are not co-linear. Hence, if the optical axis is horizontal, the visual axis is usually slightly offset from the horizon. For the purposes of this invention, the straight-ahead gaze refers to the position at which the optical axis is oriented horizontally.) Optically transmissive lower liquid 124 is present in a sufficient amount that orienting optical axis 120 in the horizontal orientation for distant vision positions optical axis 120 through lower liquid 124. Most of the anterior visual zone and the posterior visual zone of lenses 114, 116, respectively, are immersed in lower liquid 124. The anterior visual zone and posterior visual zone are typically substantially concentric about the front vertex and the rear vertex. Contact interface 123 between lower liquid 124 and upper fluid 122 is above the vertexes in the straight-ahead gaze. Preferably, lower liquid 124 is present in a sufficient amount that in the straight-ahead gaze at least 70 percent, and more preferably all, of the anterior and posterior visual zones and are immersed in lower liquid. Thus, in straight-ahead gaze, light entering prosthesis 110 travels along optical axis 120 and is primarily refracted by denser lower liquid 124 and the lenses 114, 116. It is believed that any distortion caused by the presence of the fluid interface 123 between the anterior or posterior visual zone will be minor and appear as glare to the extent it is even noticeable. The greater the portions of the visual zones that are immersed in lower liquid 124 in the straight-ahead gaze, the less likely there will be significant, if any, glare or optical aberration, such as coma or halo.

The curvatures of lenses 114, 116 are calculated to account for the refractive index of lower liquid 124 such that light traveling through eye 150 from the Punctum Remotum may be focused on macula 172. The radii of curvature of lenses 114, 116 may be selected depending upon the specific upper and lower fluids 122, 124 chosen and the desired amount of accommodation.

Figure 4:
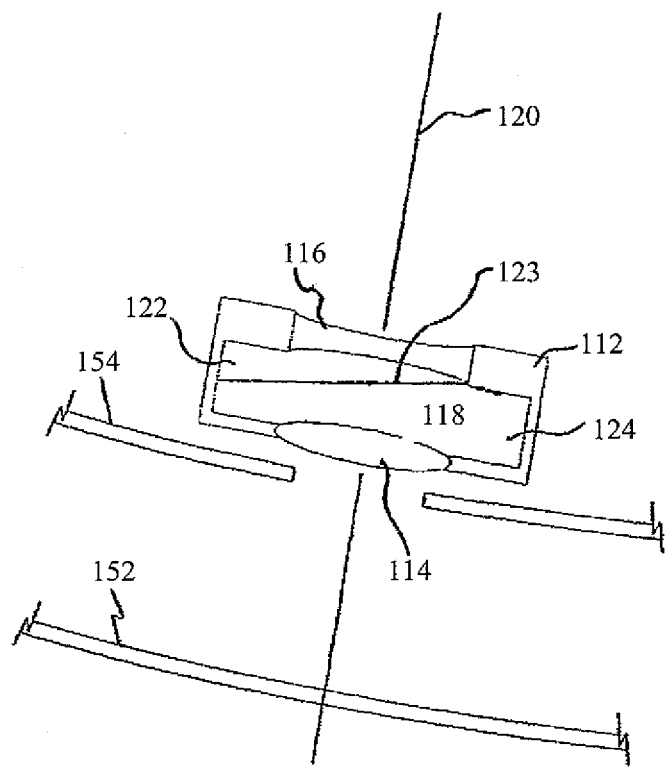
FIG. 4 is a schematic, enlarged view of the prosthesis of FIG. 3, depicting the prosthesis oriented in the reading position.
Figure 7:
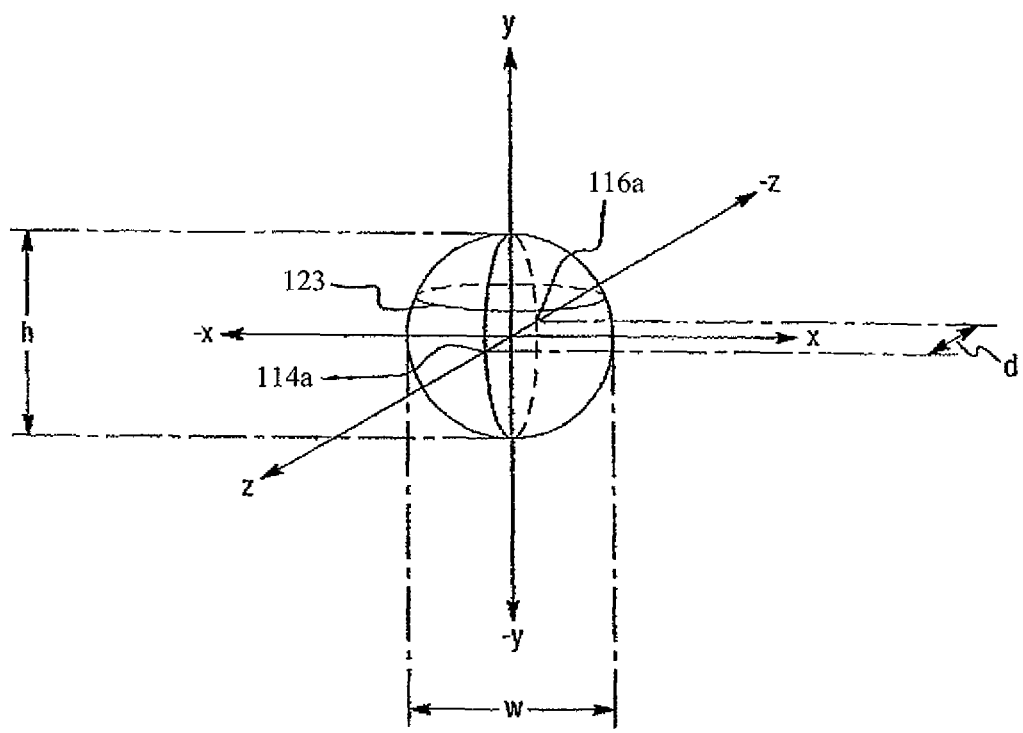
FIG. 7 is a simplified illustration of a prosthesis optic body set on a Cartesian coordinate system.

On down gaze, optical axis 120 rotates to an angle ϕ relative to the horizontal 180, as shown in FIG. 4. Referring now more particularly to FIG. 7, optic body 112 is shown in a straight-ahead gaze centered on a Cartesian coordinate system. Optic body 112 has width (w), height (h), and depth (d) on the x, y, and z-axes, respectively. In FIG. 7, optical axis 120, front vertex 114a and rear vertex 114b rest on the z-axis. Generally, the down gaze involves displacement of the optical axis relative to the horizontal or z-axis by a range of effective angles ϕ. The effective angles ϕ may comprise angles throughout a range of 70-90 degrees, throughout a range of 45-90 degrees, and in some cases throughout a range of 30-90 degrees. (It should be understood that the natural tilting movement of the human head and/or eye does not technically pivot the prosthesis about a stationary x axis.)

In the down gaze, optical axis 120 of this first embodiment is positioned at an angle ϕ relative to horizontal 180. Upper fluid 122 is present in chamber 118 in a sufficient amount that, throughout a range of effective angles ϕ, upper fluid 122 is translated down ocular lens 116 so that the optical axis 120 extends through the upper fluid 122 at the vertex of ocular lens 116. Preferably, at the range of effective angles, most of the visual zone of anterior objective lens 114 is immersed in lower liquid 124, and most of the visual zone of posterior ocular lens 116 is immersed in upper fluid 122. More preferably, at the effective angles ϕ the visual zone of anterior lens 114 has at least 70 percent of its surface area immersed in lower liquid 124. As used herein, the term "most" may encompass "all," in which case the anterior visual zone of lens 114 has 100 percent of its surface area immersed in lower liquid 124. (For the purposes of determining the percent immersed surface area, the anterior and posterior visual zones may be assumed to be those for an IOL of this invention implanted into an adult human emmetrope modeled as described in the Optical Society of America Handbook.) Simultaneously, at the effective angles ϕ the visual zone of posterior lens 116 preferably has at least 70 percent of its surface area, and more preferably all (100 percent) of its surface area, immersed in upper fluid 122. Under these conditions, incoming light rays first travel through lower liquid 124, bathing lens 114, before traveling through contact interface 123 then the upper fluid 122 bathing lens 116, before reaching retina 170. Because upper and lower fluids 122, 124 differ in refractive indices, light traveling will be refracted differently by the two fluids.

In each of the embodiments described herein, it is preferred that the substantially immiscible fluids/liquids have a sufficiently low viscosity to permit them to freely translate at substantially the same time one's gaze changes from far-to-near and near-to-far. Thus, when the head or eye is returned to straight-ahead gaze, the fluids/liquids translate back to the primary position shown in FIGS. 1 and 3. For the first embodiment, the light rays that focus on the pr pass primarily through lower liquid 124. The change in power on downgaze is created without the need for convexity change (e.g., flexing) of lenses 114, 116 or optic body 112. The change in power is also accomplished without moving prosthesis 110 relative to eye 150, i.e., towards or away from macula 172. Thus, in the first embodiment, on down gaze upper liquid 122 is displaced into the visual axis to provide the desired amount of accommodation for near, e.g., 3 to 9 inches from the eye. IOL 110 adjusts back to distance focus as straight-ahead gaze is restored.

The range of effective angles ϕ at which upper fluid 122 immerses a majority of the surface area of the posterior visual zone of lens 116 is dependent upon the relative amounts of upper fluid 122 and lower liquid 124 in chamber 118. For this first embodiment in which optical axis 120 passes through lower liquid 124 in the straight ahead gaze, the higher the level of lower liquid 124 in the chamber 118, the greater the angle φ to contact the upper fluid with the vertex of ocular lens 116. Other factors, such as lens thickness, lens radius, and volume shaping, may also affect the effective angle φ.

Referring back to FIG. 7, the width (w), height (h), and depth (d) of optic body 112 will depend upon several factors, including the sizes of the patient's physiological lens, anterior chamber, and posterior chamber. Generally, the width (w) and height (h) of optic body 112 may be, for example, in a range of 2.5 mm to 10 mm, more commonly 4.0 mm to 7.5 mm. The width (w) and height (h) are preferably, but not necessarily, the same in dimension. The depth (d) or thickness of optic body 112 should not be so great as to inhibit implantation into eye 150. On the other hand, the depth is preferably not so small as to inhibit fluid translation in chamber 118 of optic body 112. The depth (d) may be, for example, at least 0.9 mm.

Anterior visual zone of objective lens 114 and the posterior visual zone of ocular lens 116 are typically centered concentrically with the front vertex and the rear vertex. Typically, and for the purposes of embodiments of this invention, the anterior visual zone and the posterior visual zone in an average human eye are about 2 mm to 7 mm in diameter, depending upon the size of the pupil.

Although the prosthesis of this first embodiment is illustrated as an internal device implanted in posterior chamber 158 of eye 150, it is to be understood that prosthesis 110 may be implanted in the anterior chamber 156. Prosthesis 110 in anterior chamber 156 may be the sole lens in the eye, or may supplement a physiological or synthetic lens placed in posterior chamber 158. An anterior chamber implantation may be located between the cornea and the front of iris 154 or between iris 154 and the front surface of capsular bag 160. The anterior chamber implantation may be anchored to the iris or in the angle recess. As another alternative, prosthesis 110 may extend through the pupil.

Although the prosthesis of the first embodiment has been described above as an internal device or IOL, it should further be understood that prosthesis 110 may be an exterior device applied outside of the eye, for example, mounted on frames or eyeglasses in front of eye 150. Prosthesis 110 may be used in combination with a physiological or synthetic lens placed in the anterior and/or posterior chamber(s). An external prosthesis may have greater dimensions than described above, because an external prosthesis need not implantable into eye 150.

Figure 5:
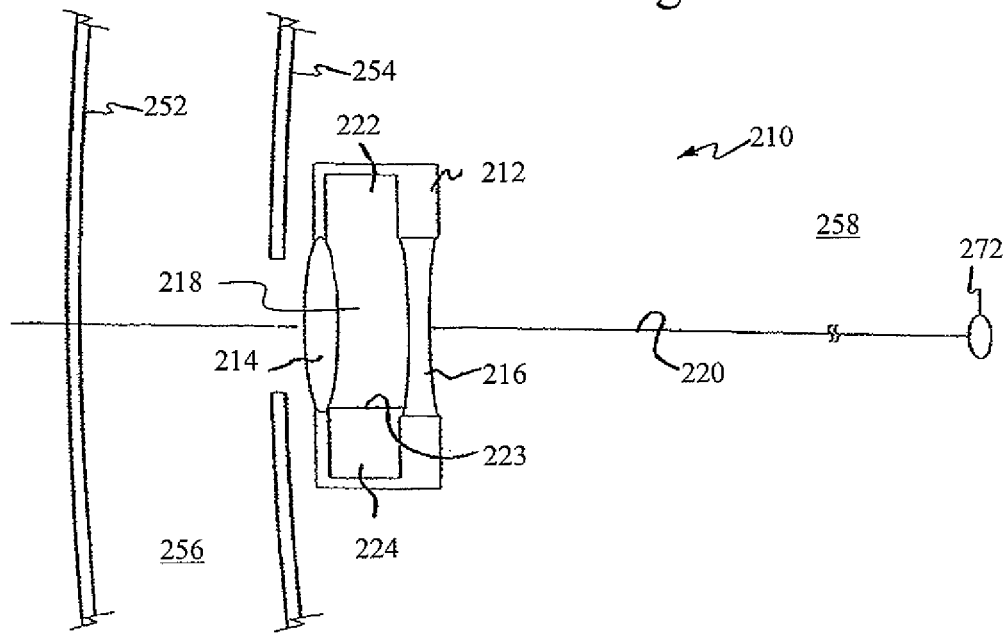
FIG. 5 is a schematic, enlarged view of a prosthesis according to a second embodiment of this invention, depicting the prosthesis in the posterior chamber of the eye oriented in a straight-ahead gaze.
Figure 6:
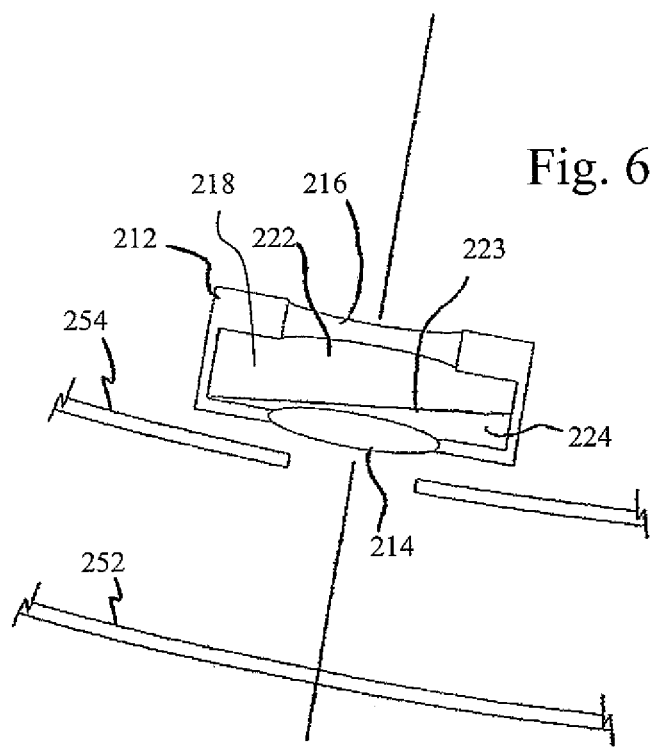
FIG. 6 is a schematic, enlarged view of the prosthesis of the second embodiment of this invention, depicting the prosthesis angled downward in a reading position.

Another prosthesis, depicted in the drawings as an intraocular lens (IOL) 210, according to a second embodiment of this invention is illustrated in FIGS. 5 and 6. As with the first embodiment, prosthesis 210 of the second embodiment comprises an optic body 212 receivable in the capsular bag of a human eye. Optic body 212 comprises a positive objective lens 214 facing the anterior side of the human eye, a negative ocular lens 216 in alignment with and spaced behind objective lens 214 to face the posterior side of the human eye. A chamber 218 is present between lenses 214, 216 within prosthesis 210. An optical axis 220 of optic body 212 intersects objective lens 214 at a front vertex and ocular lens 216 at a rear vertex.

As in the case of the first embodiment, prosthesis 210 is illustrated as an internal lens designed for placement in the posterior chamber or anterior chamber of a human eye. Alternatively prosthesis 210 may serve as an exterior device for placement outside of the human eye, in which case prosthesis 210 may be resealed and enlarged. Optical axis 220 is situated for placement in the human eye along a light path which passes through the pupil to retina 270. The light path intersects objective lens 214 at an optically transmissive anterior visual zone of lens 214, and the light intersects ocular lens 216 at an optically transmissive posterior visual zone of ocular lens 216.

FIG. 5 shows intraocular lens 210 positioned in posterior chamber 258 of the eye gazing straight ahead at the pr. In this straight-ahead gaze, optical axis 220 is parallel to the axis along the horizontal plane. Optically transmissive upper liquid 222 is present in a sufficient amount that orienting optical axis 220 in a horizontal orientation positions optical axis 220 through upper fluid 222, and most of the anterior visual zone of lens 214 and the posterior visual zone of lens 216 are immersed in the upper fluid 222. Preferably, upper fluid 222 is present in a sufficient amount that in the straight-ahead gaze at least 70 percent, and more preferably all, of the anterior and posterior visual zones of lenses 214, 216 are immersed in upper fluid 222. Thus, in straight-ahead gaze, light entering IOL 210 travels along the optical axis and is primarily refracted by upper fluid 222 and lenses 214, 216. It is believed that any distortion caused by the presence of fluid interface (i.e., plane of contact) 223 would be minor and appear as glare, to the extent it appears at all. The greater the portions of the visual zones that are immersed in upper fluid 222 in the straight-ahead gaze, the lesser the amount of glare or aberration, if any, which may occur.

The curvatures of lenses 214, 216 are calculated to account for the refractive index of upper fluid 222 such that light traveling through the eye from the Punctum Remotum may be focused on macula 272 of the eye. As described above and illustrated by way of example in FIGS. 22 and 23, various combinations of lens curvatures are possible. The radii of curvature of lenses 214, 216 may be selected depending upon the specific upper fluid 222 and lower liquid 224 chosen and the desired amount of accommodation. It is within the scope of the invention to form a lens which is capable of translating to any desired power for accommodation of eyesight, whether more (+) power or more (−) power upon down gaze.

In the down gaze, optical axis 220 of this second embodiment is positioned at an angle φ relative to horizontal to translate lower liquid 224 higher on lens 214. Lower liquid 224 is present in chamber 218 in a sufficient amount that, at the effective angles φ, optical axis 220 extends through lower liquid 224 at the front vertex and upper fluid 222 at the back vertex. Preferably, in the down gaze most of the anterior visual zone is immersed in lower liquid 224, and most of the posterior visual zone is immersed in upper fluid 222. More preferably, at the effective angles φ (e.g., 70-90 degrees, 45-90 degrees, or 30-90 degrees), the anterior visual zone of lens 214 has at least 70 percent of its area, and more preferably 100 percent of its area, immersed in lower liquid 224. Simultaneously, at the effective angles φ the posterior visual zone preferably has at least 70 percent of its area, and more preferably 100 percent of its area, immersed in upper fluid 222. Under these conditions, the light rays first travel through lower liquid 224 bathing the anterior visual zone of ocular lens 214 before traveling through contact interface 223 and upper fluid 222 bathing the posterior visual zone of ocular lens 216, thereafter reaching macula 272. Because upper fluid 222 and lower liquid 224 differ in refractive indices, upper fluid 222 and lower liquid 224 will refract the light differently.

The range of effective angles φ for displacing lower fluid 222 to contact the front vertex of objective lens 214 is dependent upon the relative amounts of upper fluid 222 and lower liquid 224 in chamber 218. For this second embodiment in which optical axis 220 passes through upper fluid 222 in the straight ahead gaze (FIG. 5), in the illustrated embodiment low levels of lower liquid 224 generally will require greater effective angles φ for contacting lower liquid 224 with the vertex of lens 214. Preferably, however, a sufficient amount of lower liquid 224 is present in this second embodiment that the bi-focal effect is realized throughout at least a range of effective angles of 70-90 degrees, especially at 90 degrees downward.

One particularly advantageous feature embodied in certain aspects of this invention is that orientation of the optical axis perpendicular to the horizon, so that the patient's head is directed straight downward at 90 degrees, causes the optical axis to pass through both the upper fluid and the lower liquid, thereby accommodating for near-sight. This advantage makes this and other embodiments of the invention having this advantage especially useful for reading.

Although prosthesis 210 of this second embodiment is illustrated as an internal lens implanted in posterior chamber 258 of the eye, it is to be understood that prosthesis 210 may be implanted in anterior chamber 256. The prosthesis in the anterior chamber may be the sole lens in the eye, or may supplement a physiological or synthetic lens placed in posterior chamber 258. Prosthesis 210 may be placed between the cornea and the iris, between the iris and the capsular bag, or through the pupil.

It should further be understood that prosthesis 210 may be an exterior device applied outside of the eye, for example, mounted on frames or eyeglasses in front of eye 250. Prosthesis 210 may be used in combination with a physiological or synthetic lens placed in the anterior and/or posterior chamber(s). Such an external prosthesis 210 may have greater dimensions than described above, since external prosthesis 210 need not be implantable into eye 250. Accordingly to yet another variation, prosthesis 210 (and other prostheses described herein) may be an intraocular lens cooperating with an external device, such as eyeglasses or contacts.

The prosthesis, including those embodiments described above and additional embodiments described below, can be used for various eye conditions and diseases, including, for example, presbyopia, aphakia, pseudophakia, anterior cortical cataract extraction (acce), posterior cortical cataract extraction (pcce), and the like. Of particular interest yet not necessarily by limitation, the intraocular lens of embodiments described herein is useful for treating retinal degenerative conditions (or "low vision"), and more particularly for reducing the effects of a scotomatous area on a visual field of a person having a retinal degenerative condition.

Figure 8:
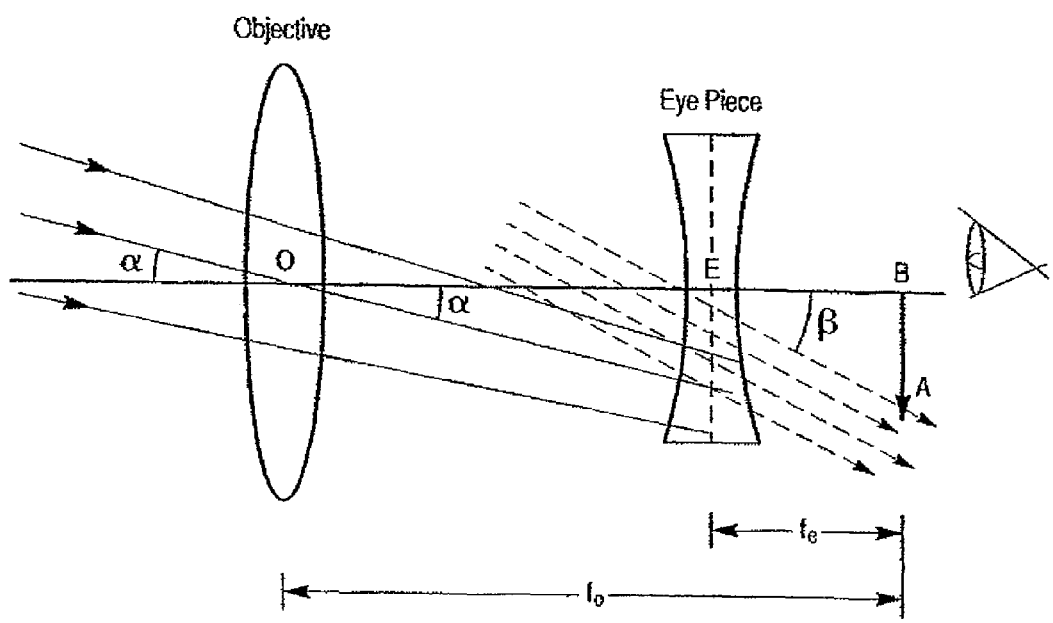
FIG. 8 shows an example of a Galilean telescopic system.

Treatment of RDCs may be accomplished by designing the prosthesis of the present invention as a Galilean-type device, wherein the objective lens of prosthesis 110, 210 is positioned in front of the ocular lens of prosthesis 110, 210 to establish a telescopic benefit and a near-magnifying benefit. The telescopic benefit is derived from the effective power of the ocular lens being calculated to be negative in power, and the objective lens in front of the ocular lens being calculated to be positive in power. The focal points and/or focal planes of the objective and ocular lenses may be coincident with one another, as is the case in a Galilean telescopic system. The combination of the negative ocular lens and positive objective lens of prosthesis 110, 210 creates a telescopic power of a Galilean type, provided the focal planes of ocular and objective are coincident, as shown in FIG. 8. As referred to herein and generally understood in the art, a "negative power" lens is a "diverging lens", i.e., a lens having a cumulative effect of diverging light passing through the lens. On the other hand, a "positive power" lens is a "converging lens", i.e., a lens having a cumulative effect of converging light rays passing through the lens. The power of the prosthesis is controlled through selection of the fluids and lens curvatures. By controlling the negative power of the ocular lens and the positive power of the objective lens, a desired magnification can be obtained. In the straight-ahead gaze, the overall telescopic effect of the ocular and objective lens preferably is negative. In the downward gaze, the prosthesis provides a near point Galilean low vision magnifier.

The telescopic effect of this embodiment reduces the effects of a scotomatous area of an individual afflicted with a RDC in straight ahead and down gazes. Without wishing to necessarily be bound by any theory, it is believed that the telescopic optics established by embodiments particularly useful in the treatment of RDCs enlarge the image desired to be viewed beyond the borders of the damaged region of the retina (and more particularly the macula) which is responsible for the scotoma, into healthy areas of the central retina. As a consequence, although the scotomatous area is not removed from the field of vision, the viewed object is shifted, magnified, or otherwise moved so that a greater percentage of the object is viewed outside of the scotoma.

While certain embodiments are described in relation to producing a telescopic effect, it is to be understood that the embodiments described herein may be practiced without providing a telescopic effect. In such non-telescopic embodiments, the lens curvatures and fluids optionally may be selected to increase the power of the lens in down gaze so that the image is enlarged beyond the borders of the damaged region of the retina, for example, in the event that the prosthesis is selected for a user afflicted with macular degeneration. For persons not having macular degeneration or similar RDCs, such as a person undergoing cataract extraction or accommodative restorative surgery for presbyopes, the power of down gaze may be selected for near point accommodation pp.

The curvatures of the lenses of the prosthesis and the fluids are selected to provide a desired overall power in straight ahead and down gaze. For example, for refractive correction surgery, it is preferably to provide a power of about 12 and about 25 diopters in straight ahead gaze (based on the number of diopters required to provide emmetropia), with the target typically being approximately 20 diopters. Adjustment of the lens power by modification of the optic body curvature is within the purview of those having ordinary skill in the art. On down gaze, the prosthesis may be provided with, for example, 1.0 to 4.0 diopter (e.g., 2.0 to 3.0 diopter) additional power, although more or less additional power is possible. It is within the scope of the invention to form a lens which is capable of translating to any additional desired power for accommodation of eyesight, whether more (+) power or more (−) power upon down gaze.

According to an exemplary embodiment of the invention in which telescopic power is desired, for example potentially in the treatment of a person with macular degeneration, the prosthesis is provided with about 1.0× to about 5.2× magnification (e.g., about 1.5× to about 5.0×). More preferably, in straight ahead gaze the magnification is about 1.5× to about 3.0×, and in down gaze the magnification is about 2.0× to about 5.0× (e.g., about 3.0× to about 5.0×) by selection of an appropriate secondary fluid. The higher the magnification, the smaller the user's field of view and, therefore, a balance must be reached. Preferably, this balance is dictated by the patient's pupil size, and in particular, maximizing the field of view for the particular pupil size. The greater amount of the pupillary area the internal prosthesis can fill without introducing an opaque housing into the pupillary line of sight, the better the field of view will appear to the user. Determination of suitable ocular and objective lenses for a particular magnification is within the purview of those skilled in the art. Generally, the focal length of the objective divided by the focal length of the eyepiece equals the magnifying power of the telescope.

In internal lens embodiments of the invention, the iris of the natural eye in essence functions as the outer "housing" of the telescope, thereby removing the need for combining the intraocular lens with an artificial opaque housing, such as those used in conventional telescopic devices. Advantageously, omission of an artificial ocular outer housing can improve the field of vision of a person afflicted with a RDC. For example, the artificial housing of a telescope typically is sized and positioned away from the iris in such a manner as to limit the field of vision. That is, the field of vision for a telescope is smaller than the field of vision obtainable by the naked eye because the naked eye is not constrained by a peripheral housing. Further, the artificial housing of a telescope is not able to account for subtle variations in pupil size due to pupil dilation (e.g., for far vision) and pupil restriction (e.g., for near vision). In embodiments of the present invention in which the iris functions as the telescopic housing (in terms of view of vision) of the internal intraocular lens, the user's field of view is not unduly restricted.

Figure 9:
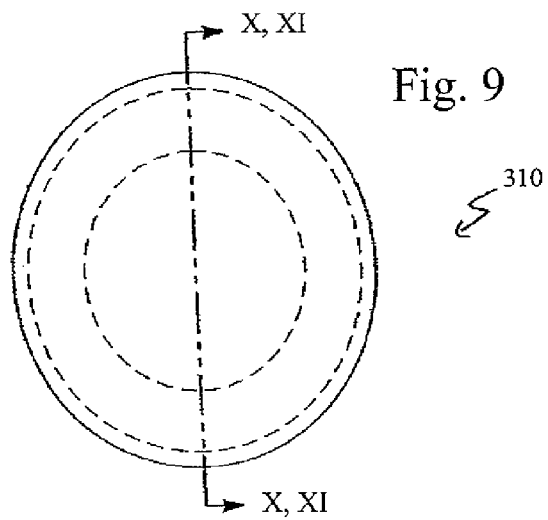
FIG. 9 is a front view of modified embodiments of the prosthesis.
Figure 10:
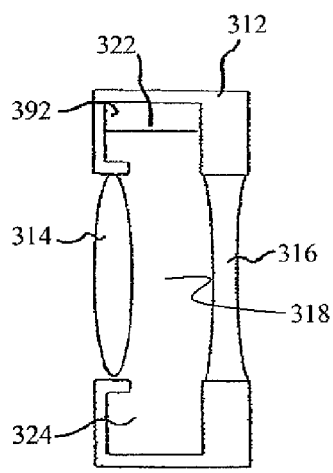
FIGS. 10 and 11 are side sectional views of FIG. 9 according to respective modified embodiments of the invention.
Figure 11:
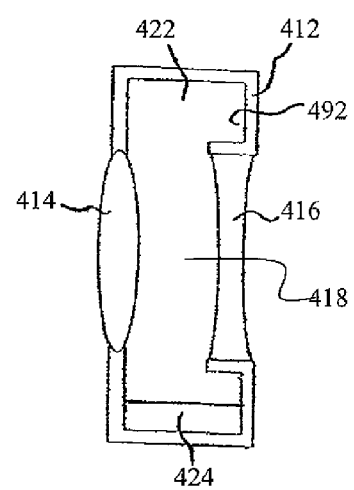

Examples of modifications suitable for the first and second embodiments and falling within the scope of this invention are illustrated in FIGS. 9-11. In the interest of brevity and for the purpose of elaborating upon the structure, functions, and benefits of these modifications, the above descriptions of the first and second embodiments are incorporated herein and not repeated in their entireties.

In the first embodiment illustrated in FIGS. 3 and 4, when the eye is tilted upward by a sufficient angle, upper fluid 122 may come into contact with lens 114, including where optical axis 120 intersects lens 114, causing accommodation from far to near vision. In some instances this effect may be inconsequential or even desirable to the prosthesis user, depending upon the preferences of the user. However, other prosthesis users may wish to maintain accommodation for far vision at gazes upward of the horizontal orientation, to as high as $\phi=-90°$, i.e., to vertical. For convenience, these modified embodiments of FIGS. 9-11 are illustrated with the lens curvatures of FIGS. 3 and 4. It should be understood that other curvature combinations, including but not limited to those shown in FIGS. 22 and 23, may be employed in these modified embodiments.

In accordance with the modification illustrated in FIGS. 9 and 10, a prosthesis 310 includes a biconvex positive objective lens 314, a biconcave negative ocular lens 316, and a chamber 318 between lenses 314, 316 within optic body 312. Chamber 318 is enclosed between lenses 314, 316 and optic body 312, and more particularly is enclosed by a structure consisting of lenses 314, 316, and body 312. Lenses 314, 316 are preferably spherical as shown in FIG. 9, although each may be aspheric. The front of optic body 312 includes a fluid displacement zone in the form of, for example, an annular channel or trench 392, which constitutes part of chamber 318. In the illustrated embodiment, channel 392 extends 360° around the perimeter of the front interior of body 312. It is to be understood that channel 392 may extend only a portion of the way around the perimeter of the front interior of body 312, in which case channel 392 is preferably arcuate. Chamber 318 includes an upper fluid 322 and a lower liquid 324. As prosthesis 310 is tilted upward into its vertical position, upper fluid 322 of lower density is maintained in channel 392, out of contact with lenses 314, 316. In this manner, in upward gaze the optical path to the retina passes through lower liquid 324 while substantially avoiding upper fluid 322. In downward gaze, the optical path extends through lower fluid 324 at objective lens 314 and upper fluid 322 at objective lens 316.

In the second embodiment illustrated in FIGS. 5 and 6, when the eye is tilted upward by a sufficient angle, lower liquid 224 may enter into the optically visual zone of ocular lens 216, causing accommodation from far to near vision. In some instances this effect may be inconsequential or even desirable to the prosthesis user, depending upon the preferences of the user. However, some prosthesis users may wish to maintain accommodation for far vision at gazes upward of the horizontal orientation, to as high as $\phi=-90°$, i.e., to vertical.

Prosthesis 410 shown in FIG. 11 comprises a biconvex positive objective lens 414, a biconcave negative ocular lens 416, and a chamber 418 between lenses 414, 416 within optic body 412. Chamber 418 is preferably enclosed between lenses 414, 416 and body 412, and more preferably is enclosed by a structure consisting of lenses 414, 416, and body 412. Lenses 414, 416 are preferably spherical as shown in FIG. 9, although each may be aspheric. The rear of body 412 includes a fluid displacement zone illustrated as annular channel or trench 492, which constitutes part of chamber 418. In the illustrated embodiment, channel 492 extends 360° around the perimeter of the rear interior of optic body 412. It is to be understood that channel 492 may extend only a portion of the way around the perimeter of the rear interior of optic body 412, in which case channel 492 is preferably arcuate. Chamber 418 includes an upper fluid 422 and a lower liquid 424. As prosthesis 410 is tilted upward into its vertical position, lower fluid 424 of higher density is maintained in channel 492, displaced out of contact with lenses 414, 416. In this manner, the optical path to the retina passes through upper liquid 422 while substantially avoiding lower fluid 424, thereby preserving the distance viewing in upward gaze. In downward gaze, the optical path extends through lower fluid 424 at objective lens 414 and upper fluid 422 at objective lens 416, thereby providing the desired bi-focal effect.

Other designs and configurations may also be practiced for channeling or displacing the secondary fluid away from the optical centers when the optic body is tilted upward relative to the horizontal position. For example and not necessarily limitation, the haptics may be provided with a channel that communicates with the lens chamber, or an internal wall.

Figure 15:
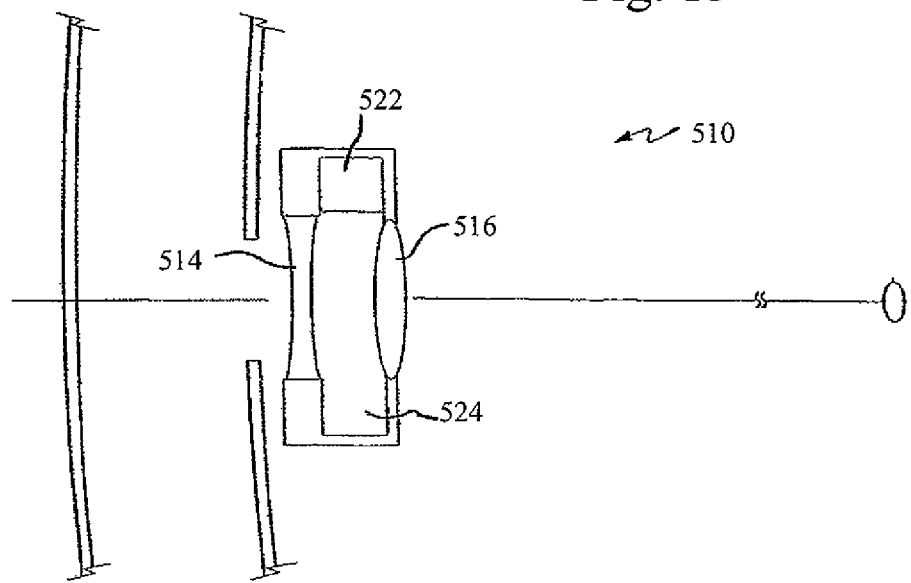
FIG. 15 is a schematic, enlarged view of the prosthesis of a third embodiment of the invention, depicting the prosthesis oriented in straight-ahead gaze.
Figure 16:
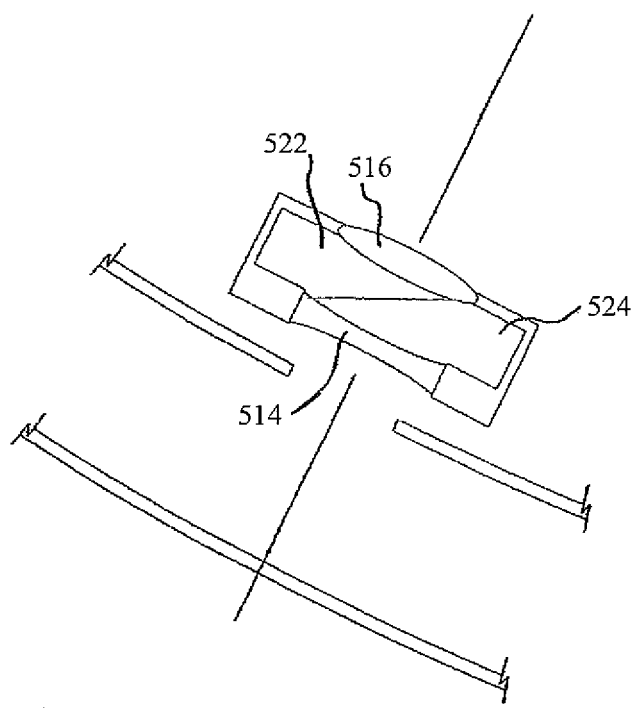
FIG. 16 is a schematic, enlarged view of the prosthesis of FIG. 15, depicting the prosthesis oriented in the reading position.

FIGS. 15 and 16 show an alternative embodiment of the invention in which intraocular lens 510 is inverted or reversed, so that objective lens 514 is negative and ocular lens 516 is positive. This embodiment is especially useful in the treatment of retinitis pigmentosa, glaucoma, and other disorders in which reverse magnification is desired for improving vision of the user. FIGS. 15 and 16 show lower fluid 524 as the primary fluid, i.e., so that lower fluid 524 is intersected by the optical axis and upper fluid 522 is not intersected by the optical axis during straight ahead view. It should be understood that this embodiment may be modified to select upper fluid 522 as the primary fluid. Translation of the fluids as caused by head movement is generally the same as discussed above with respect to FIGS. 1-6. Reversing the optics of a Galilean magnifier expands a user's field of view, which is particularly useful for treatment of conditions that restrict the user's field of view, such as glaucoma and retinitis pigmentosa (RP).

Many modifications and variations to the embodiments and examples described herein are within the scope of the invention. An example of a modified embodiment containing modifications suitable for other embodiments described herein is illustrated in FIGS. 17-20. In the interest of brevity and for the purpose of elaborating upon the structure, functions, features, and benefits of this modification, the descriptions of the embodiments, including the first and second embodiments and the Galilean and reverse Galilean systems described above, and the various additional curvature combinations as exemplified in FIGS. 22 and 23 and otherwise described, are incorporated herein and not repeated in their entirety.

In accordance with this modification, an intraocular lens 610 further comprises at least one internal plate (or baffle) 690. Internal plate 690 may comprise, for example, a rigid material or a flexible material, such as a film. Internal plate 690 preferably is optically transmissive, and more preferably transparent. Plastics such as polymethmethacrylate (PMMA) are especially useful materials from which internal plate 690 may be made.

Internal plate 690 preferably is non-lenticular, and preferably has substantially flat, substantially parallel opposite sides to contribute substantially no refractive power to prosthesis 610. Internal plate 690 preferably is arranged substantially perpendicular to optical axis 620, although internal plate 690 may be skewed slightly at an oblique angle from perpendicular, e.g., no more than about 20 degrees, preferably no more than 10 degrees, to change the fluid mechanics and alter the effective downward angle at which the bi-focal or near vision comes into view. For example, the skew angle may range from ±0.1 to ±5 degrees, more specifically ±0.5 to ±2 degrees, still more specifically about ±0.5 degrees relative to perpendicular from optical axis 620.

A first side of internal plate 690 is spaced apart from positive lens 614 to define a first (anterior) compartment of a first volume. A second side of internal plate 690 is spaced apart from negative lens 616 to define a second (posterior) compartment of a second volume. The first and second volumes may be the same or different relative to one another. For example, the anterior and posterior compartments may be provided with different volumes by installing internal plate 690 closer to either positive lens 614 or negative lens 616, and/or by skewing internal plate 690 as described above.

Figure 20:
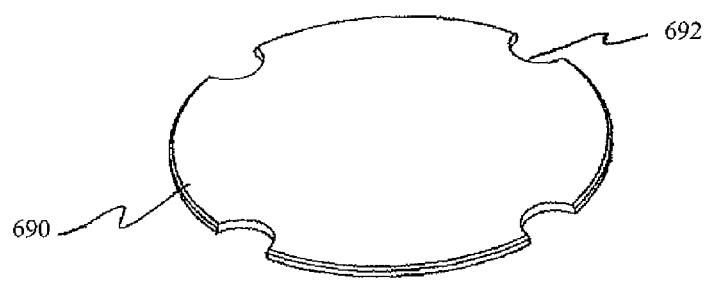

Internal plate 690 includes fenestrations or passageways 692 to place the anterior and posterior compartments in fluid communication with one another, thereby allowing the flow of fluids 622, 624 between the compartments, for example, when prosthesis 610 is tilted. As best shown in FIG. 20, fenestrations 692 may comprise one, two, or more grooves or indentations situated about the outer periphery of internal plate 690. Fenestrations 692 may possess alternative shapes than shown; for example, fenestrations 692 may comprise holes spaced from the periphery of internal plate 690. Preferably, at least one fenestration 692 is located in the upper half of internal plate 690, such as at the top of internal plate 690, and at least one fenestration 692 is located in the lower half, such as at the bottom of internal plate 690. In the illustrated embodiment, two fenestrations 692 are located in the upper half and two fenestrations 692 are located in the lower half of internal plate 690. Fenestrations 692 are shown spaced equal distances from one another about the periphery of internal plate 690. It should be understood that the upper and lower halves of internal plate 690 may contain the same or a different amount of fenestrations 692 relative to the other, and that internal plate 690 may contain fewer or more fenestrations 692 than shown.

Figure 19:
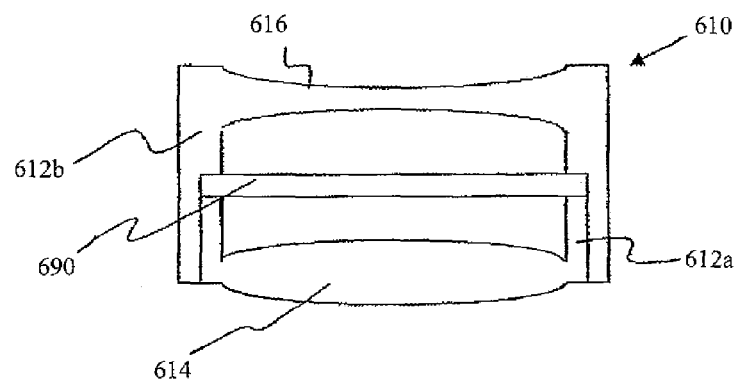

Internal plate 690 is retained inside optic body 612 using any suitable mechanism and method. Preferably, internal plate 690 is installed in a fixed and stationary position relative to lenses 614, 616. By way of example, internal plate 690 may have an outer periphery that is mounted to the inside of optic body 612, as best shown in FIG. 19. In FIG. 20, optic body 612 includes a first case structure 612a connected to positive lens 614 and a second case structure 612b connected to negative lens 616. It should be understood that lenses 614, 616 do not need to be positive and negative, respectively. Further, curvatures other than biconcave and biconvex may be selected. Other curvature combinations are depicted in FIGS. 22 and 23.

Case structures 612a, 612b possess cylindrical flanges extending towards one another. When assembled, the flange of first case structure 612a is positioned radially inward of and mates with the flange of second case structure 612b. Internal plate 690 rests on a shoulder of second case structure 612b, and is retained in place by the end of the cylindrical flange of first case structure 612a. Fenestrations located about the periphery of internal plate 690 have a radial dimension that is greater than the width of the shoulder of second case structure 612b so that at least a portion of fenestrations remains exposed to permit the flow of fluid therethrough.

A hermetic seal may be established at the mating interface of case structures 612a, 612b by fusing the case materials or applying an adhesive. Although not shown, a gasket also may be included, for example on the shoulder of second case structure 612b to create or supplement the hermetic seal. Other modifications not shown may also be implemented. For example, internal plate 690 may optionally include an internal chamber for holding a liquid or gas. Alternatively, webs or filaments may be used for suspending internal plate 690 in a fixed position.

Figure 17:
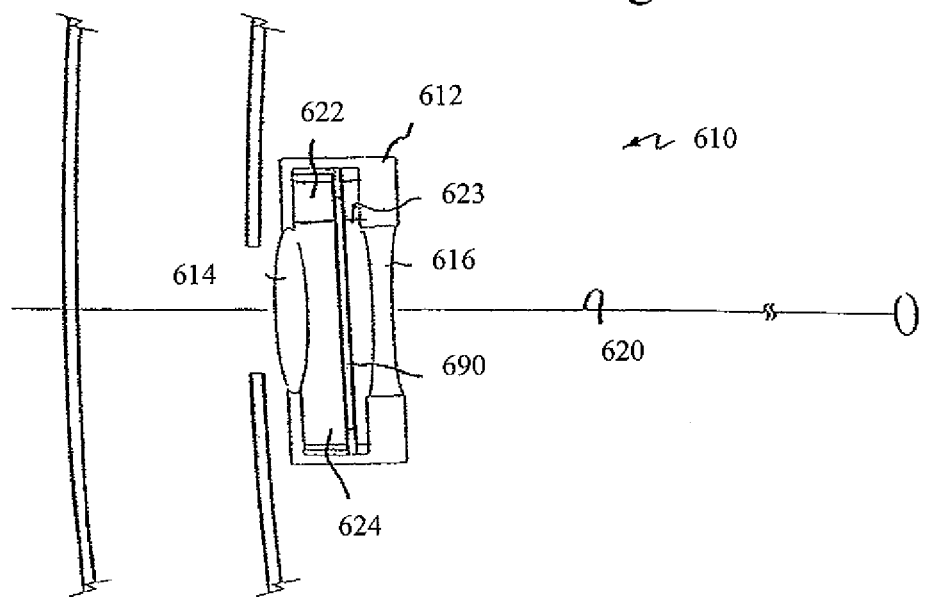
FIGS. 17-20 are schematic views of another modification and modified embodiment.

As shown in FIG. 17, optically transmissive lower liquid 624 is present in a sufficient amount that orienting the optical axis horizontally positions the optical axis through lower liquid 624, bathing most of the anterior visual zone and the posterior visual zone in lower liquid 624, so that optical axis 620 intersects lower liquid 624 but not upper fluid 622, which may be a liquid, gas, or vacuum. Optical axis 620 passes through the internal plate 690 in this modified embodiment. Contact interface 623 between lower liquid 624 and upper fluid 622 is displaced away from optical axis 620 in the embodiment illustrated in FIG. 17. It should be understood that the embodiment of FIG. 17 can be modified to select the upper fluid as the primary fluid, as shown in FIGS. 5 and 6.

Figure 18:
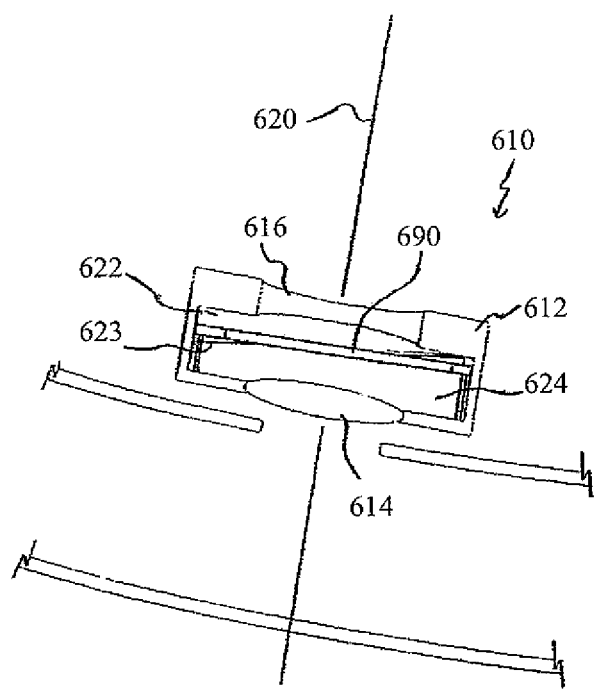

In the down gaze shown in FIG. 18, optical axis 620 of this modified embodiment is positioned at an angle relative to horizontal to translate lower liquid 624 on positive lens 614 and upper fluid 622 on negative lens 616. Upper fluid 622 is present in the chamber in a sufficient amount that, throughout a range of effective angles φ, optical axis 620 extends through upper fluid 622 at the vertex of negative lens 616. Preferably, at the range of effective angles, most of the surface area of the anterior visual zone is immersed in lower liquid 624, and most of the posterior surface area of the posterior visual zone is immersed in upper fluid 622. Upper fluid 622 and lower liquid 624 flow through fenestrations 692 to redistribute upper fluid 622 mostly in the posterior compartment and lower liquid 624 mostly in the anterior compartment.

Under these conditions, the light rays first travel through lower liquid 624 before traveling through upper fluid 622. However, in this modified embodiment the optical axis does not intersect through the contact interface 623. Rather, the light passes through internal plate 690, which displaces contact interface 623 away from and preferably out of the visual field, thereby eliminating or substantially eliminating contact interface 623 from the visual field. As a consequence, to the extent that a meniscus described in the first and second embodiments above may contribute to glare or aberration, if any, internal plate 690 eliminates or substantially reduces the glare or aberration.

Internal plate 690 may be translated (shifted) towards either lens 614, 616 and/or skewed (tilted) as described above to assist in reducing the effect of or eliminating contact interface 623 from the visual field. For example, in FIGS. 17 and 18, in which the lower liquid 624 is the primary fluid, internal plate 690 is offset from center of the chamber towards posterior lens 616. The first compartment between positive lens 614 and the anterior surface of internal plate 690 has a greater volume than the second compartment between negative lens 616 and the posterior side of internal plate 690. Optionally, the volume of the first compartment is approximately equal to the volume of lower liquid 624, and the volume of the second compartment is approximately equal to the volume of upper fluid 622. Upon downgaze, the upper fluid partially or completely fills the second compartment, and the lower fluid partially or completely fills the first compartment. In the event that the upper liquid is the primary fluid, internal plate 690 may be shifted and/or skewed towards anterior lens 614.

Figure 21:
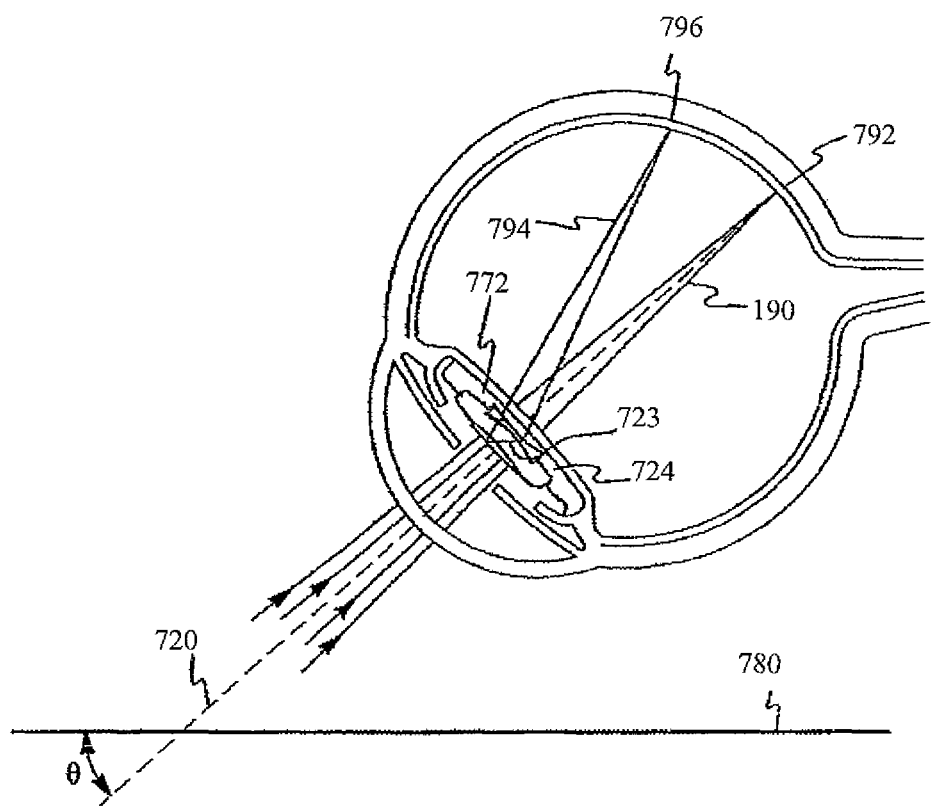
FIG. 21 is a schematic view of still another embodiment of the invention.

According to another embodiment of the invention shown in FIG. 21, within the range of effective downward angles $\phi$ relative to the horizontal plane 780, the eye passes through an intermediate downward gaze at which the fluid interface 723 creates a prismatic effect for splitting light rays from a viewed object or objects into a first set of light rays 790 for producing a first locus of fixation at a first retinal region 792 and a second set of light rays 794 for producing the second locus of fixation at a second retinal region 796. Angles associated with the intermediate downward gaze are typically encountered at the transition from the straight-ahead view to the downward gaze. The first and second retinal regions are preferably different from one another, and more preferably are mutually exclusive, i.e., non-overlapping. At least one and optionally both of the first and second retinal regions 792, 796 falls partially or completely outside of a damaged macular region responsible for producing the scotoma. For example, the first retinal region 792 may comprise an area along the visual axis and thus may overlay the damaged macular region responsible for the scotomatous area, whereas the second retinal region 796 receiving light rays 794 as a result of the prismatic effect may lie in a more functional region outside of the damaged macular region responsible for the scotomatous area.

The range of angles $\phi$ associated with the intermediate downward gaze is dependent upon the relative amounts of the upper fluid 722 and lower liquid 724 in the chamber. For the embodiment in which the optical axis passes through the lower liquid in the straight ahead gaze, the higher the level of the lower liquid in the chamber, the greater the angle $\phi$ to cause the prismatic effect. Other factors, such as lens thickness, lens radius, and volume shaping may also affect the angle $\phi$. Generally, the range of angles $\phi$ associated with the prism effect are within (and optionally throughout) a range of 30-60 degrees. The anterior and posterior lenses may be spherical or aspheric. Aspheric lenses may compensate for astigmatism, coma, and higher order aberrations. It should be understood that this aspect of the invention may be practice with embodiments of the invention comprising a fluid interface in the line of sight.

Methods of making optic bodies are well known in the art and are described throughout the literature. These methods, which are suitable for use with the various aspects of the present invention, include, not necessarily by limitation, molding and lathing, with injection molding being perhaps the most commonly employed and well known of these methods. The formation of a molded body with an internal chamber is well known in the injection molding and lathing arts. Methods of gel-capsule manufacture as applied in the pharmaceutical industry may also be applied, as these methods describe introduction of fluids into capsules without leaving vacuum or air space within the capsule. As mentioned above, the anterior and posterior lens may be made as a unitary piece, or separately then joined together, such as by adhesive, fusion, or the like.

The optic body and lenses preferably comprise a material or materials biologically compatible with the human eye, and capable of injection molding, lathing, or the like. In particular, the materials are preferably non-toxic, non-hemolytic, and non-irritant. The optic body and lenses preferably are made of a material that will undergo little or no degradation in optical performance over its period of use. Unlike a contact lens, however, the material does not have to be gas permeable, although it may be. For example, the optic body may be constructed of rigid biocompatible materials, such as, for example, polymethylmethacrylate, or flexible, deformable materials, such as silicones, deformable acrylic polymeric materials, hydrogels and the like which enable the optic body to be rolled, deformed, or folded for insertion through a small incision into the eye. The above list is merely representative, not exhaustive, of the possible materials that may be used in this invention. For example, collagen or collagen-like materials, e.g., collagen polymerized with a monomer or monomers, may be used to form the optic body. However, it is preferred to make the optic body of a material or materials, e.g., elastic, adapted for folding or deformation to facilitate insertion of the prosthesis into the eye when so desired.

The prosthesis surface may be modified with heparin or any other type of surface modification designed to increase biocompatibility and decrease possibility of the formation of capsular haze. The prosthesis may also include a "ledge" for reducing formation of capsular haze. Additionally, the lenses may be treated, e.g., with a fluorinated substance, and made more or less hydrophilic/hydrophobic to create the desired fluidic motion and limit the adherence of the fluid to the lenses, thereby shortening transition time as gravity changes power from straight ahead to down gaze and back.

The prosthesis of this invention may include haptics, which are generally shown in FIGS. 1 and 2, in which the haptics are designated by reference numeral 190. Haptics generally serve to anchor the optics body in place in the eye. Haptics are usually attached directly to the lens body. Various types of haptics are well known in the art, and their incorporation into this invention would be within the purview of an ordinary artisan having reference to this disclosure. Generally, the typical haptic is a flexible strand of nonbiodegradable material fixed to the lens body. By way of example, suitable haptics for this invention may be made of one or more materials known in the art, including polypropylene, poly(methyl methacrylate), and any biocompatible plastic or material in use now or in the future that are used to hold the lens in place. The haptics used with invention may possess any shape or construction adapted or adaptable for use with this invention for securing the lens body in place in the eye. In the posterior chamber, the haptics secure the optical lens within the capsular bag, whereas in the anterior chamber haptics may extend into the area defined between the anterior iris and posterior cornea. For anterior chamber intraocular lenses, it is also within the scope of this invention to use an "iris claw", which hooks onto the fibers of the iris, or anterior chamber angle fixed haptics.

The upper and lower fluids may be introduced and retained in the optic body chamber prior to implanting or otherwise applying the prosthesis to a human eye. The upper and lower fluids may be introduced into the chamber by any technique consistent with the objects of this invention. For example, a syringe or the like may be used for injecting the upper fluid and lower liquid into the chamber. Optionally, an entry port may be provided in the optic body for introducing the upper fluid and lower liquid into the chamber of the optic body. The entry port may be formed during injection molding, by penetrating the optic body with a suitable hole-making instrument, such as a drill or pin, or it may established by the injecting instrument, e.g., syringe, during introduction of the fluids. The location of the entry port is not critical. Other techniques may also be used to form the optic body.

It is within the scope of the method of this invention to provide the optic body with a vent port for expelling gas (usually air) from inside the optic body chamber as the upper and lower fluids are introduced through the entry port. The vent may be separate from the entry port, or may consist of the entry port such that gas entrapped in the chamber is expelled as the upper and lower fluids are introduced into the chamber. Alternatively, the chamber may be evacuated prior to the introduction of the upper fluid and the lower liquid. Subsequent to introducing the upper and lower fluids into the chamber, the entry port and optional vent may be sealed to enclose the chamber in a known manner, such as by fusion or plugging with a compatible material, which may be the same or different than the material of which the optical body is comprised.

It is within the scope of this invention to insert the prosthesis body into the human eye, then to subsequently inject a portion or all of the upper fluid and the lower liquid into the implanted prosthesis body in situ. The benefit to this latter variation is that an IOL body that is not filled with fluids/liquids is more amenable to folding and deformation during implantation.

Both upper fluid and the lower liquid are preferably optically transmissive. It also is preferred that, when the fluids are emulsified by shaking or a position change, minimal mixing of the upper fluid and the lower liquid occur, and whatever mixing does occur quickly separates out again. The substantially immiscible upper fluid and lower liquids are preferably optically transparent. It is within the scope of the invention for one or more of the optically transmissive fluids to possess a tint of any color that is not dense enough to significantly impede the transmission of light or the intended objects of this invention. It is within the scope of this invention for the upper fluid to be in the form of a liquid, gas or vacuum. Thus, the term "fluid" as used herein encompasses the use of liquid, gas (e.g., air), or vacuum.

The multi-focal prosthesis of the invention is not limited to the use of only two fluids/liquids in the prosthesis. Three or more fluids of different refractive indexes can be used to create a multi-power, multifocus prosthesis so that objects between far (pr) and near (pp) can be focused upon more clearly. Tri-focals of this invention preferably have three liquids of different densities, with the refractive index of the fluids differing with fluid density.

Fluids that may be used for in the prosthesis body include, but are not limited to, those common to ophthalmic surgery, such as the following: water, aqueous humor, short-chain silicone oils, hyaluron, viscoelastics, polydimethyl siloxane, bis-phenyl propyl dimethicone, phenyl tri-methicone, di-phenyl-di-methyl siloxane copolymer (vinyl-terminated), cyclopentasiloxane, phenyl trimethicone, polydimethyl methyl phenyl siloxane, polymethyl phenyl siloxane, liquid chitosan, heparin, perfluoro-n-octane (perfluoron), perfluoroperhydrophenanthrene, perfluoromethyldecalin, perfluoropentane, perfluoro-1,3-dimethyl cyclohexane, perfluorodecalin, perfluoroperhydro-p-fluorene, and glycerine. It is preferable, but not necessary, that one of the fluids used in the prosthesis of this invention is water, such as distilled water, to save cost and hazards of broken or ruptured intraocular lenses in vivo.

Many other fluorocarbon liquids may be selected for use as the lower liquid and/or the upper fluid. Representative fluorocarbon fluids that may be used for providing the desired refractive properties of this invention include haloalkanes. Representative haloalkanes that may be useful include trichloromonofluoromethane, dichlorodifluoromethane, monochlorotrifluoromethane, bromotrifluoromethane, dichloromonofluoromethane, monochlorodifluoromethane, dichlorotetrafluoroethane. Other fluorocarbons include 2,2,2-trifluoroethanol, octofluoropentanol-1, dodecafluoroheptanol-1. Other liquids include methanol, acetonitrile, ethyl ether, acetone, ethanol, methyl acetate, propionitrile, 2,2 dimethyl butane, isopropyl ether, 2-methyl pentane, ethyl acetate, acetic acid, D-mannitol, and D-sorbitol.

Many polymethyl/silicon liquid species can be used, including, by way of example, the following: tetrachlorophenylsilsesquixane-dimethyl siloxane copolymer, poly(methylsilsesquioxane, 100% methyl), poly(methylhydridosilsesquioxane, 90%), poly(phenylsilsesquioxane), 100% phenyl, poly(phenyl-methylsilsesquioxane 90% phenyl 10% methyl), dimethicone copolyol PPG-3 oleyl ether (aka alkyl polyether), hydroxymethyl acetomonium PG dimethicone (aka betaine), amino propyl dimethicone (aka amine).

It is within the scope of this invention to select two or more different liquids or fluids as the upper fluid, and to select two or more different liquids as the lower liquid. Dilution of miscible liquids of different indices of refraction may be effective for tailoring the refractive index of the upper fluid or lower liquid phase. Additionally, the dilution of salts, sugars, etc. into the liquids may modify the refractive index. Examples of aqueous salts include sodium chloride, calcium chloride, zinc chloride, potassium chloride, and sodium nitrate (referred to herein as "NaN"). Generally, the concentration of the salts and sugars should be no higher than their saturation points.

These represent chemicals that may be safe within the eye. Unsafe chemicals, i.e., that are not biologically compatible with the eye, are less desirable but can have the same visual outcome if maintained within the optical cavity and not exposed to the ocular media within the eye.

The prosthesis can be inserted into the posterior chamber of the human eye, preferably into the capsular bag posterior to the iris to replace the physiological (natural) lens in the capsular bag positioned using known equipment and techniques. Posterior implantation is preferred because, among other reasons, this is the location from which the physiological lens is removed. By way of example, intra-capsular cataract extraction and IOL implantation utilizing clear corneal incision (CCI), phacoemulsification or similar technique may be used to insert the intraocular lens after the physiological crystalline lens has been removed from the capsular bag. The incision into the eye may be made by diamond blade, a metal blade, a light source, such as a laser, or other suitable instrument. The incision may be made at any appropriate position, including along the cornea or sclera. It is possible to make the incision "on axis", as may be desired in the case of astigmatism. Benefits to making the incision under the upper lid include reduction in the amount of stitching, cosmetic appeal, and reduced recovery time for wound healing. The prosthesis is optionally rolled or folded prior to insertion into the eye, and may be inserted through a small incision, such as on the order of about 3 mm. It is to be understood that as referred to in the context of this invention, the term "capsular bag" includes a capsular bag having its front surface open, torn, partially removed, or completely removed due to surgical procedure, e.g., for removing the physiological lens, or other reasons. For example, in FIGS. 1 and 2 capsular bag 160 has an elastic posterior capsule, and an anterior capsular remnant or rim defining an opening through which the physiological lens was removed.

Alternatively, the prosthesis may be inserted in the anterior chamber between the cornea and the iris. In an anterior chamber implant, the prosthesis is generally situated forward of, or mounted to, the iris.

Selection of appropriate fluids can be determined with the assistance of Snell's Law and is based on the Index of Refraction (IR) of the media. When light rays pass between non-opaque media, there is a mathematical description of how light is bent, or refracted. Different non-opaque media have their own specific index of refraction, and mixed media take on their own individual index of refraction. If two media are placed in contact with one another but do not mix, light will be refracted as it travels from the first medium into the second medium. If a third medium is provided, the light will be refracted again as it passes between the second and third media.

The prosthesis of the various aspects and embodiments described herein may be used in one or both eyes of the subject. For example, it may be desirable to have the prosthesis serve as a telescope in one eye, but not the other.

EXAMPLES

All examples were modeled on the Zemax Version 10.0 optical design program, SE edition, from Focus Software, Inc.

The human eye was first modeled as a typical or schematic adult human emmetrope, as described in the Optical Society of America Handbook. Each of the models described below is for a posterior chamber IOL design. The following assumptions were made for the human eye for the purposes of the calculations. The model was assumed to have spherical surfaces only (whereas the real cornea and lens are actually aspherics). Each structure of the schematic human eye was assumed to be made of a material having a uniform or homogenous index (whereas in the real human eye, the index of refraction may vary somewhat through each structure of the eye). The model also assumed that the capsular bag walls were very thin and parallel, i.e., non-existent. The lens was assumed to have symmetric radius, i.e., spherical. The pr was assumed to be 10 meters. Three wavelengths with equal weighting were used for optimization and evaluation: 510 nm, 560 nm, and 610 nm to provide a simple approximation of the human photopic response. Walker, Bruce H., Optical Design for visual Systems, SPIE Press (2000). The Abbe wavelength dispersion is assumed to be 55.0 for all natural materials. The indices at other wavelengths were calculated based on $n_D$ and the dispersion value. Modeling was performed for small pupil sizes of 1.5 mm. The initial values assumed for the eye are listed below in Table 1.

TABLE 1

| Surface | Radius (mm) | Thickness (mm) | Refr. Index (@589 nm) | Material |
|---|---|---|---|---|
| Anterior Cornea | 7.80 | 0.55 | 1.3771 | Cornea |
| Posterior Cornea | 6.50 | 3.05 | 1.3374 | Aqueous Humor |
| Anterior Lens | 10.20 *20.83** | 4.00 | 1.4200 | Natural lens |
| Posterior Lens | −6.00 *−4.26** | 16.6 *16.80** | 1.3360 | Vitreous Humor |
| Retina | *−12.67** | | | |

*italics indicates values optimized through Zemax program, under assumed conditions as listed.

The above assumptions and conditions were maintained for the IOL designs, with the natural lens replaced by the IOL. The overall length of the eye models was kept constant. The IOL thickness was allowed to adjust during optimization, but not to exceed 4.0 mm.

Figure 12:
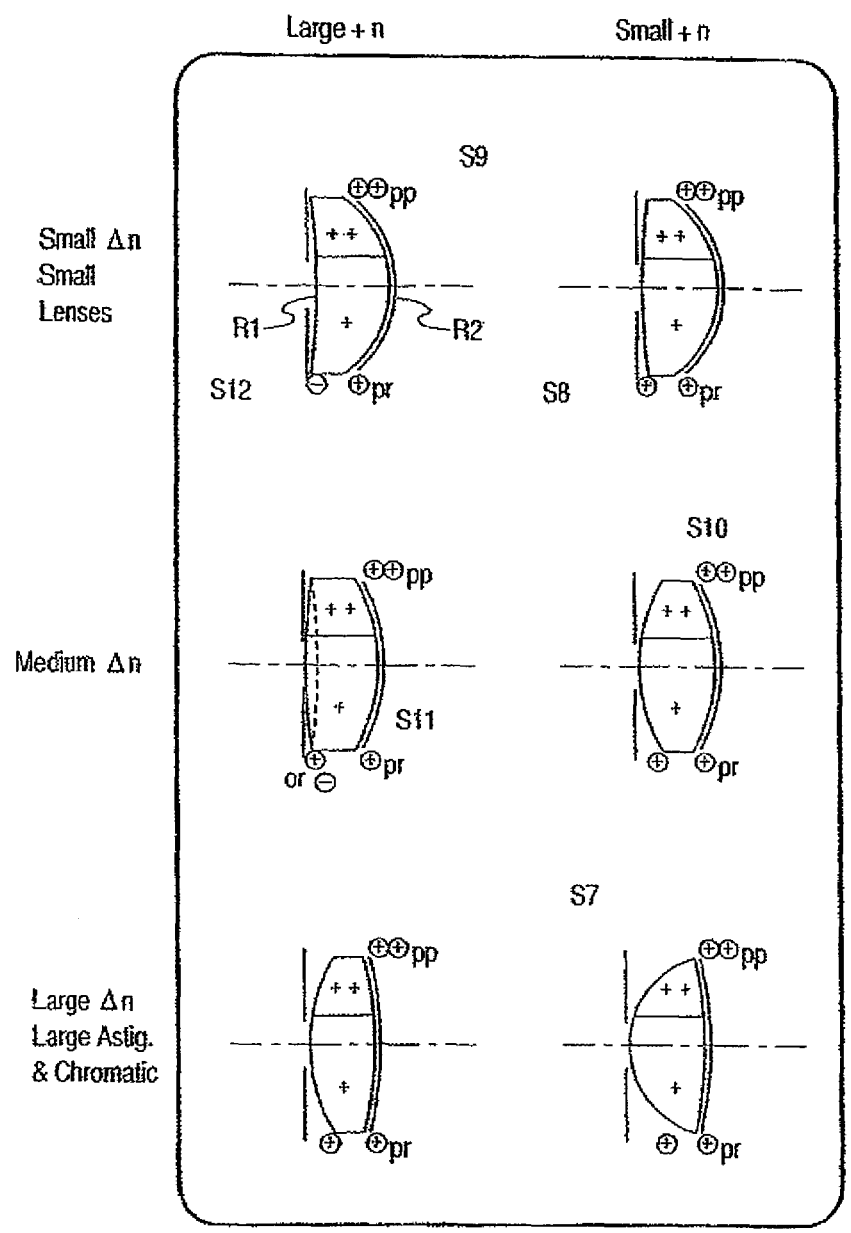
FIGS. 12-14 relate to examples reported below.

According to one set of IOL designs illustrated in FIG. 12, the lower liquid is the primary liquid and has a lesser refractive index than the upper liquid. Accordingly, in this embodiment the upper liquid has a greater refractive index and imparts accommodative power (+power) on down gaze by increasing the effective power of the posterior IOL surface. Models were made for the combinations of fluids in Table 2. The index of refraction value were either taken as reported in the literature at 37° C. (body temperature) in a saturated solution, or were estimated based on calculations using three (3) wavelengths (of 510 nm, 560 nm, and 610 nm).

TABLE 2

| Label | Lower Liquid | Upper Liquid | $n_D1$** | $n_D2$** | R1*** | R2*** | Thickness**** |
|---|---|---|---|---|---|---|---|
| S9 | Aq-NaN | PDMS- (37° C.) | 1.38543 | 1.39908 | −43.750 | −2.52 | 2.12 |
| S8 | Aq-NaCl | PDMS (37° C.) | 1.37794 | 1.39908 | 6.081 | −3.65 | 2.32 |
| S12 | Aq-CaCl | Mineral Oil | 1.44287 | 1.46408 | −14.770 | −3.98 | 1.62 |
| S10 | Aq-KCl | PDMS- (37° C.) | 1.36035 | 1.39908 | 1.875 | −6.82 | 1.58 |
| S11 | Aq-ZnCl | Mineral Oil | 1.40229 | 1.46408 | 5.837 | −9.00 | 3.54 |
| S7 | Aq-NaCl | Mineral Oil | 1.37789 | 1.46408 | 3.029 | −14.00 | 2.30 |

**$n_D1$ and $n_D2$ are refractive index of lower liquid and the upper liquid, respectively, at or about its saturation limit at 589 nm wavelength.
***R1 and R2 are the radius of curvature of the anterior surface and the posterior surface, respectively, in millimeters.
****Lens thickness was measured in millimeters.

The shapes of the anterior and posterior walls were calculated for hypothetical cases by modifying the adult human emmetrope model to simulate an IOL. The crystalline lens material was replaced with the lower fluid to simulate horizontal pr gaze (at 10 m), and the pp (250 mm) was modeled in a directly vertical 90° downward gaze angle using two liquids with the interface perpendicular to the optical axis. The posterior radius of the lens was selected to obtain the needed change of power with the upper liquid introduced to accommodate for pp (at about 250 mm) Other assumptions listed above for the model eye were also made. Gaze angles of less than 90° were then evaluated without re-optimizing the model parameters. Specifically, gaze angles of 50° and 70° were investigated. The 90°, 70°, and 50° gaze angles were each evaluated at the following five field points of 0°, ±7.5°, and ±15°. The root mean square (RMS) of each spot radius value was then recorded. Reported below are the averages of the five field values, and the RMS for the on-axis) (0° field point. All RMS values are in microns.

TABLE 3

| Label | RMS Spot: Average of 5 Fields | | | RMS Spot: On-Axis Value | | |
|---|---|---|---|---|---|---|
| | 90° | 70° | 50° | 90° | 70° | 50° |
| S9 | 4.81 | 5.14 | 7.26 | 3.87 | 4.47 | 6.97 |
| S8 | 4.78 | 4.89 | 7.93 | 3.21 | 4.00 | 8.16 |
| S12 | 4.03 | 4.03 | 5.94 | 2.88 | 3.11 | 5.31 |
| S10 | 9.28 | 9.45 | 15.59 | 5.16 | 6.84 | 15.71 |
| S11 | 5.41 | 6.164 | 17.95 | 3.45 | 5.86 | 18.99 |
| S7 | 7.29 | 8.79 | 26.29 | 4.53 | 8.37 | 27.67 |

Smaller RMS values generally indicate less aberration and better focus on the retina. Generally, values less than 7.00 microns are preferred for the assumed conditions.

The IOL schematics are laid out as though plotted on a chart, with the actual fluid's refractive index along the horizontal axis (abscissa) and the difference in the index values of the two fluids on the vertical axis (ordinate). Internal to the lens schematics, the fluids are labeled with the following symbols:

+ a liquid having an index of refraction greater than the humors in which the IOL is immersed when implanted;

++ a liquid having an index of refraction greater than the humors and the adjacent "+" liquid;

− a liquid having an index of refraction lower than the humors;

−− a liquid having an index of refraction lower than the humors and the adjacent "−" liquid.

The cornea (not shown) is to the left of the IOL schematics, and the iris is shown immediately to the left of the IOL schematics. The surface that produces the optical power change (pr to pp adaptation) is shown with a double line.

Fluid combinations S9 and S10 were less preferred due to the steep curvatures of R1 (anterior surface) or R2 (posterior surface).

Figure 13:
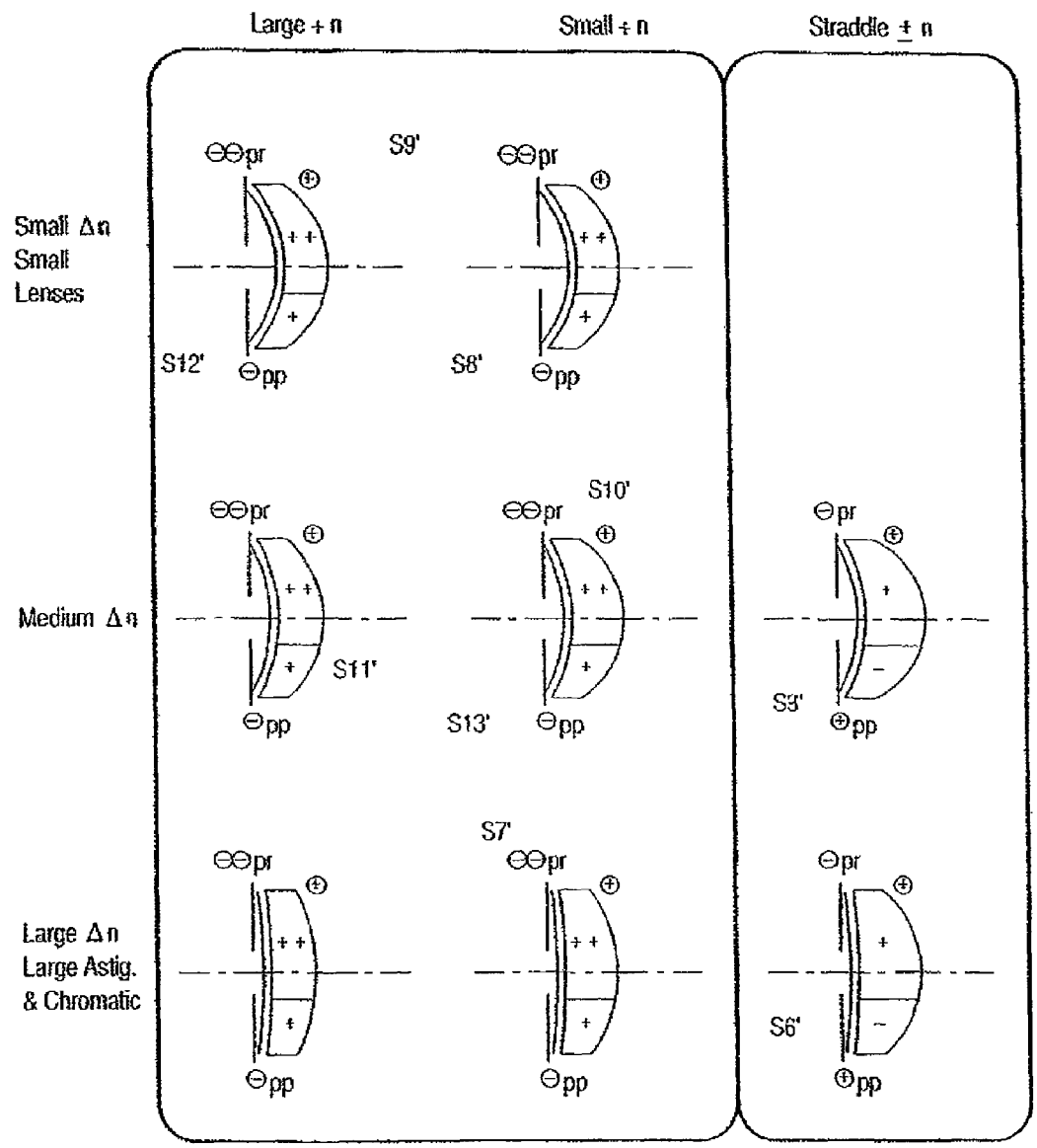

According to another set of IOL designs illustrated in FIG. 13, the upper liquid is the primary liquid and has a greater refractive index than the lower liquid. Hence, the lower liquid imparts accommodative power (+power) on down gaze by increasing the effective power of the lens. Models were made for the following combinations of fluids:

TABLE 4

| Label | Lower Liquid | Upper Liquid | $n_D1$ | $n_D2$ | R1 | R2 |
|---|---|---|---|---|---|---|
| S9' | PDMS- (37° C.) | Aq-NaN | 1.39908 | 1.38543 | −2.90 | −1.703 |
| S8' | PDMS (37° C.) | Aq-NaCl | 1.39908 | 1.37794 | −4.40 | −2.032 |
| S12' | Mineral Oil | Aq-CaCl | 1.46408 | 1.44287 | −4.45 | −2.770 |
| S10' | PDMS- (37° C.) | Aq-KCl | 1.39908 | 1.36035 | −8.10 | −2.458 |
| S11' | Mineral Oil | Aq-ZnCl | 1.46408 | 1.40229 | −12.95 | −4.296 |
| S13' | Mineral Oil | Aq-NaN | 1.46408 | 1.38543 | −16.50 | −4.564 |
| S7' | Mineral Oil | Aq-NaCl | 1.46408 | 1.37789 | −18.17 | −4.661 |
| S5' | PDMS (37° C.) | Water (37° C.) | 1.39908 | 1.33100 | −14.35 | −2.760 |
| S6' | Mineral oil | Water (37° C.) | 1.46408 | 1.33100 | −28.40 | −5.032 |

The shapes of the anterior and posterior walls were calculated for hypothetical cases by modifying the adult human emmetrope model to simulate an IOL. The crystalline lens material was replaced with the upper fluid to simulate horizontal pr gaze (at 10 m), and the pp (at about 250 mm) was modeled in a directly vertical 90° downward gaze angle using two fluids with the interface perpendicular to the optical axis. The anterior radius of the lens was selected to obtain the needed change of power with the lower liquid introduced to accommodate for pp. Again, assumptions made above for the model eye were applied, as needed. Gaze angles of less than 90° were then evaluated without re-optimizing the model parameters.

TABLE 5

| Label | RMS Spot: Average of 5 Fields | | | RMS Spot: On-Axis Value | | |
|---|---|---|---|---|---|---|
| | 90° | 70° | 50° | 90° | 70° | 50° |
| S8' | 7.06 | 7.17 | 8.61 | 6.23 | 6.38 | 7.77 |
| S12' | 5.88 | 5.91 | 6.55 | 4.56 | 4.69 | 5.55 |
| S10' | 5.24 | 5.54 | 10.67 | 4.23 | 4.82 | 10.20 |
| S11' | 4.03 | 4.73 | 13.33 | 2.73 | 3.92 | 12.78 |
| S13' | 3.94 | 5.18 | 17.23 | 2.58 | 4.40 | 16.47 |
| S7' | 3.97 | 5.59 | 13.60 | 2.63 | 4.87 | 18.25 |
| S5' | 4.66 | 5.80 | 17.64 | 3.54 | 5.26 | 17.10 |
| S6' | 4.11 | 8.39 | 31.63 | 2.68 | 7.74 | 30.06 |

Fluid combinations S5', S8', S9', S10', and S12' were less preferred due to the small sizes of the IOL R1 and/or R2.

Figure 14:
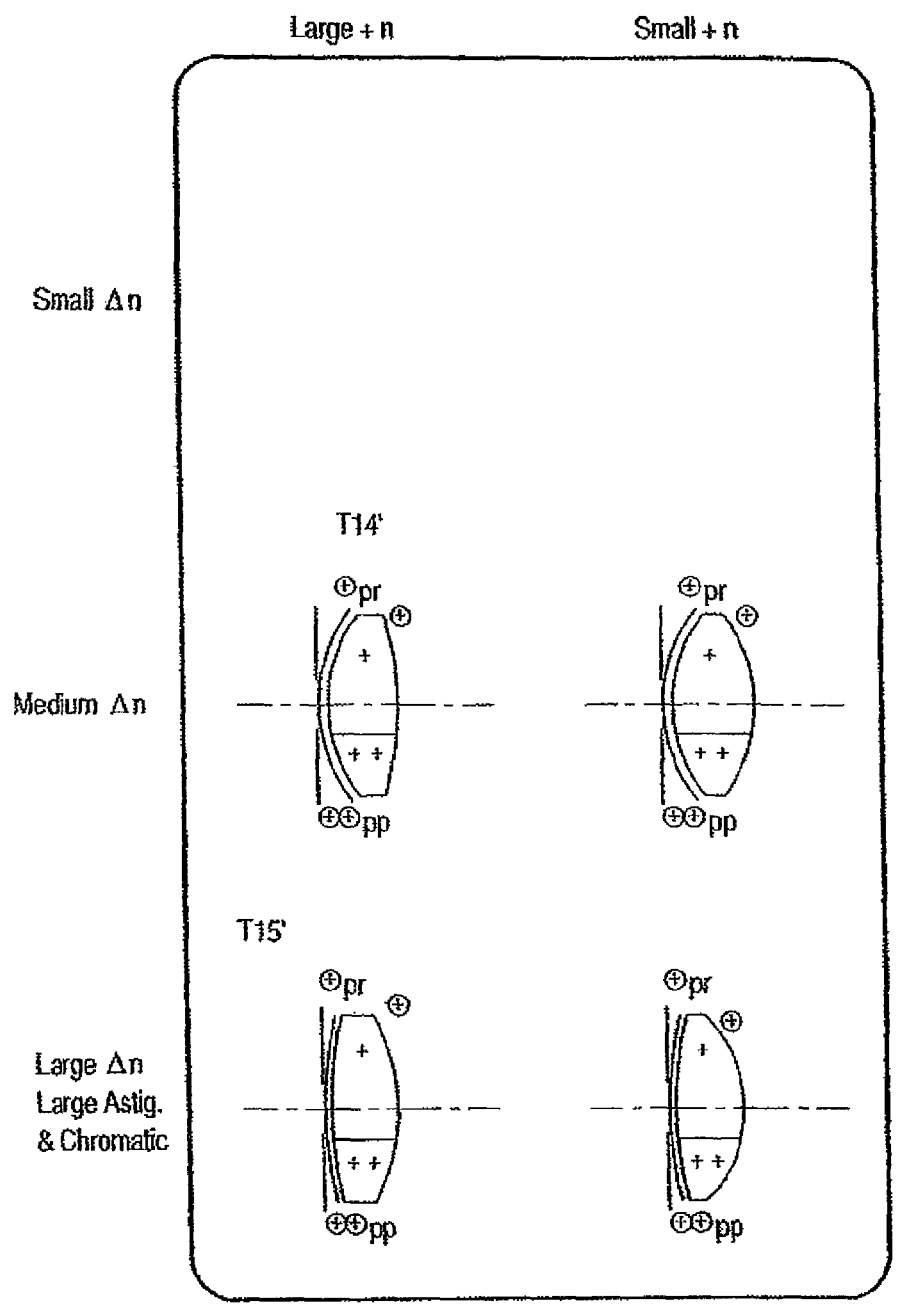

According to another set of IOL designs illustrated in FIG. 14, the upper liquid is the primary liquid and has a smaller refractive index than the lower liquid. Models were made for the combinations of fluids set forth in Table 6, with the corresponding results reported in Table 7:

TABLE 6

| Label | Lower Liquid | Upper Liquid | nD1 | nD2 | R1 | R2 |
|---|---|---|---|---|---|---|
| T14' | PDMS- (37° C.) | Aq-CaCl | 1.39908 | 1.44287 | 9.19 | −4.750 |
| T15' | PDMS (37° C.) | Glycerol | 1.39908 | 1.47238 | 15.30 | −4.022 |

TABLE 7

| Label | RMS Spot: Average of 5 Fields | | | RMS Spot: On-Axis Value | | |
| --- | --- | --- | --- | --- | --- | --- |
| | 90° | 70° | 50° | 90° | 70° | 50° |
| T14' | 5.14 | 7.31 | 19.56 | 3.34 | 4.43 | 14.81 |
| T15' | 4.65 | 8.29 | 28.38 | 3.04 | 5.24 | 23.17 |

It was observed from modeling that the tilt of the fluid interface (downward gazes not equal to 90°) may cause astigmatism and chromatic aberrations, which can be minimized by decreasing the differential value between the fluid indices. However, too small an index differential may require compensation vis-à-vis reduction to the radii of curvature. Reduction in radii of curvature may produce IOLs have diameters that are too small and increased spherical aberration and coma. Thus, a fundamental tradeoff exists between the normal aberrations (no tilt of the fluids) and the performance as the gaze departs from directly downward.

The lens schematics illustrated in the accompanying drawings are intended to show general trends, and are not intended or shown as precise designs. The illustrated schematics are also not intended to be exhaustive of the scope of possible IOL body designs within the scope of this invention. For example, it may be desirable for some applications to design the anterior and posterior lenses as both positive or as both negative, or to provide either or both of the lenses without power. The complete disclosure of U.S. Pat. No. 6,855,164 to Glazier is incorporated herein by reference. While many of the above embodied methods have been explained in reference to a human subject, it should be understood that the subject may be an animal, e.g., for testing or veterinarian purposes.

The foregoing detailed description of the preferred embodiments of the invention has been provided for the purposes of illustration and description, and is not intended to be exhaustive or to limit the invention to the precise embodiments disclosed. The embodiments were chosen and described in order to best explain the principles of the invention and its practical application, thereby enabling others skilled in the art to understand the invention for various embodiments and with various modifications as are suited to the particular use contemplated. It is intended that the scope of the invention cover various modifications and equivalents included within the spirit and scope of the appended claims.

What is claimed is:

1. A prosthesis, comprising:
an anterior lens;
a posterior lens spaced from the anterior lens and aligned with the anterior lens along an optical axis, at least one of the anterior lens and the posterior lens having curvature providing positive or negative power;
an optic body supporting the anterior lens and the posterior lens in spaced relation to one another to establish a chamber between the lenses;
an optically transmissive primary fluid and an optically transmissive secondary fluid contained in the chamber of the optic body, the primary fluid having a first density and a first refractive index, the secondary fluid having a second density and a second refractive index that differ from the first density and the first refractive index, respectively, the primary and secondary fluids positioned in the chamber such that orienting the optical axis in a horizontal orientation for far vision positions the optical axis through the primary fluid but not the secondary fluid; and
a non-lenticular internal plate positioned within the chamber between the anterior and posterior lenses, wherein the internal plate has planar, parallel opposite surfaces facing the anterior and posterior lenses, respectively, to contribute no power to the prosthesis, the opposite surfaces of the internal plate being spaced from the anterior and posterior lenses such that orienting the optical axis for near vision at a range of effective downward angles relative to the horizontal orientation positions the optical axis to extend through the primary fluid on one side of the internal plate and the secondary fluid on an opposite side of the internal plate.

2. The prosthesis of claim 1, wherein said range of effective downward angles comprises at least an angle of 90 degrees relative to the horizontal orientation at which the optical axis extends through the primary fluid and the secondary fluid on the opposite sides of the internal plate.

3. The prosthesis of claim 1, wherein the primary fluid and the secondary fluid comprise a liquid and a gas.

4. The prosthesis of claim 3, wherein the gas comprises air.

5. The prosthesis of claim 1, wherein the first density is greater than the second density.

6. The prosthesis of claim 1, wherein the second density is greater than the first density.

7. The prosthesis of claim 1, wherein the primary and secondary fluids share a contact interface, and wherein the internal plate displaces the contact interface away from the optical axis throughout the range of effective downward angles.

8. The prosthesis of claim 1, wherein the internal plate has fenestrations.

9. The prosthesis of claim 1, wherein the opposite surfaces of the internal plate are offset at an oblique angle relative to a plane oriented perpendicularly to the optical axis.

10. The prosthesis of claim 1, wherein the opposite surfaces of the internal plate are offset at an angle of less than about +20 degrees relative to a plane oriented perpendicularly to the optical axis.

11. The prosthesis of claim 1, wherein the opposite surfaces of the internal plate are offset at an angle of +0.1 to +5 degrees relative to a plane oriented perpendicularly to the optical axis.

12. The prosthesis of claim 1, wherein the opposite surfaces of the internal plate are offset at an angle of +0.5 to +2 degrees relative to a plane oriented perpendicularly to the optical axis.

13. The prosthesis of claim 1, wherein the internal plate partitions the chamber into an anterior compartment and posterior compartment of unequal volume.

14. A method for optically altering an image, comprising:
viewing an object through the prosthesis of claim 1.

15. A prosthesis, comprising:
a positive lens having curvature providing positive power;
a negative lens having curvature providing negative power, the negative lens spaced from the positive lens and aligned with the positive lens along an optical axis;
an optic body supporting the positive lens and the negative lens in spaced relation to one another to establish a chamber between the lenses;
an optically transmissive primary fluid and an optically transmissive secondary fluid contained in the chamber of the optic body, the primary fluid having a first density and a first refractive index, the secondary fluid having a second density and a second refractive index that differ from the first density and the first refractive index, respectively, the primary and secondary fluids positioned in the chamber situated such that orienting the optical axis in a horizontal orientation for far vision positions the optical axis through the primary fluid but not the secondary fluid; and a non-lenticular internal plate positioned within the chamber between the positive and negative lenses, wherein the internal plate has planar, parallel opposite surfaces facing the positive and negative lenses, respectively, to contribute no power to the prosthesis, the opposite surfaces of the internal plate being spaced from the anterior and posterior lenses such that orienting the optical axis for near vision at a range of effective downward angles relative to the horizontal orientation positions the optical axis to extend through the primary fluid on one side of the internal plate and the secondary fluid on an opposite side of the internal plate.

16. The prosthesis of claim 15, wherein said range of effective downward angles comprises at least an angle of 90 degrees relative to the horizontal orientation at which the optical axis extends through the primary fluid and the secondary fluid.

17. The prosthesis of claim 15, wherein the primary fluid and the secondary fluid comprise a liquid and a gas.

18. The prosthesis of claim 15, wherein the positive and negative lenses are arranged with respect to one another to collectively establish a Galilean system.

19. The prosthesis of claim 15, wherein the opposite surfaces of the internal plate are offset at an oblique angle relative to a plane oriented perpendicularly to the optical axis.

20. The prosthesis of claim 1, wherein the internal plate has a top and a bottom, wherein the top of the internal plate is spaced relative to the optic body to provide at least a first passageway and the bottom of the internal plate is spaced from the optic body to provide at least a second passageway, the first and second passageways permitting for the movement of the primary and secondary fluids therethrough during tilting movement of the prosthesis from far vision to near vision.

21. The prosthesis of claim 15, wherein the internal plate has a top and a bottom, and wherein the top of the internal plate is spaced from the optic body to provide at least a first passageway and the bottom of the internal plate is spaced from the optic body to provide at least a second passageway, the first and second passageways permitting for the movement of the primary and secondary fluids therethrough during tilting movement of the prosthesis from far vision to near vision.

22. The prosthesis of claim 1, wherein the internal plate is off-center so as to be positioned in closer proximity to one of the anterior and posterior lenses than to the other.

23. The prosthesis of claim 15, wherein the internal plate is off-center so as to be positioned in closer proximity to one of the positive and negative lenses than to the other.

* * * * *